US011298218B2

(12) United States Patent
Montgomery et al.

(10) Patent No.: US 11,298,218 B2
(45) Date of Patent: Apr. 12, 2022

(54) EMBOLIC FILTER SYSTEM

(71) Applicant: W. L. Gore & Associates, Inc., Newark, DE (US)

(72) Inventors: William D. Montgomery, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 96 days.

(21) Appl. No.: 16/478,712

(22) PCT Filed: Jan. 19, 2018

(86) PCT No.: PCT/US2018/014395
§ 371 (c)(1),
(2) Date: Jul. 17, 2019

(87) PCT Pub. No.: WO2018/136724
PCT Pub. Date: Jul. 26, 2018

(65) Prior Publication Data
US 2019/0374328 A1 Dec. 12, 2019

Related U.S. Application Data
(60) Provisional application No. 62/488,802, filed on Jan. 20, 2017.

(51) Int. Cl.
*A61F 2/01* (2006.01)
(52) U.S. Cl.
CPC ............ *A61F 2/013* (2013.01); *A61F 2/0105* (2020.05); *A61F 2/011* (2020.05); *A61F 2/014* (2020.05);
(Continued)

(58) Field of Classification Search
CPC .......... A61F 2/01; A61F 2/013; A61F 2/0105; A61F 2002/016; A61F 2002/018;
(Continued)

(56) References Cited

U.S. PATENT DOCUMENTS 5,152,777 A   10/1992   Goldberg et al.
5,569,184 A * 10/1996   Crocker .................... A61F 2/88
                                              604/103.01
(Continued)

FOREIGN PATENT DOCUMENTS

CN   110680459 A    1/2020
EP     1594419 A1  11/2005
(Continued)

OTHER PUBLICATIONS

International Preliminary Report on Patentability received for PCT Patent Application No. PCT/US2012/059769, dated May 1, 2014, 10 pages.
(Continued)

*Primary Examiner* — Vi X Nguyen

(57) ABSTRACT

Various aspects of the present disclosure are directed toward an embolic filter system. The embolic filter system generally includes a filter and an elongated element. In some examples, the elongate element extends to a position distal to a proximal end of the filter and operates to protect against medical devices entangling with the filter. In some examples, the elongate element is soft and compliant and operates with a hemostatic seal to provide for a hemostatic seal within a lumen of the elongate element while maintaining the lumen as a working lumen through which medical devices can be passed.

11 Claims, 15 Drawing Sheets

(52) U.S. Cl.
CPC ... *A61F 2002/016* (2013.01); *A61F 2002/018* (2013.01); *A61F 2230/0067* (2013.01); *A61F 2230/0069* (2013.01); *A61F 2250/0024* (2013.01); *A61F 2250/0039* (2013.01)

(58) Field of Classification Search
CPC ...... A61F 2250/0039; A61F 2250/0024; A61F 2250/0023; A61B 2017/2215
See application file for complete search history.

(56) References Cited

U.S. PATENT DOCUMENTS

| | | |
|---|---|---|
| 5,649,906 A | 7/1997 | Gory et al. |
| 6,179,859 B1 | 1/2001 | Bates et al. |
| 6,273,900 B1 | 8/2001 | Nott et al. |
| 6,361,545 B1 | 3/2002 | Macoviak et al. |
| 6,440,120 B1 | 8/2002 | Maahs |
| 6,468,291 B2 | 10/2002 | Bates et al. |
| 6,676,683 B1 | 1/2004 | Addis |
| 6,942,681 B2 | 9/2005 | Johnson |
| 7,083,633 B2 | 8/2006 | Morrill et al. |
| 7,344,515 B2 | 3/2008 | Coyle |
| 7,585,309 B2 | 9/2009 | Larson |
| 7,648,495 B2 | 1/2010 | Bates |
| 7,771,452 B2 | 8/2010 | Pal et al. |
| 7,803,168 B2 | 9/2010 | Gifford et al. |
| 7,837,702 B2 | 11/2010 | Bates |
| 7,972,361 B2 | 7/2011 | Corcoran et al. |
| 8,257,384 B2 | 9/2012 | Bates |
| 8,545,552 B2 | 10/2013 | Garrison et al. |
| 8,702,744 B2 | 4/2014 | Bates |
| 8,728,113 B2 | 5/2014 | Bates |
| 8,753,370 B2 | 6/2014 | Lashinski |
| 8,876,796 B2 | 11/2014 | Fifer et al. |
| 9,186,238 B2 | 11/2015 | Eidenschink et al. |
| 9,220,615 B2 | 12/2015 | Denison et al. |
| 9,314,605 B2 | 4/2016 | Arcaro et al. |
| 9,498,225 B2 | 11/2016 | Zhadkevich |
| 9,526,864 B2 | 12/2016 | Quick |
| 9,526,865 B2 | 12/2016 | Quick |
| 9,561,347 B2 | 2/2017 | Holm et al. |
| 9,839,540 B2 | 12/2017 | Armstrong et al. |
| 9,913,740 B2 | 3/2018 | Perko |
| 9,943,397 B2 | 4/2018 | Bonnette et al. |
| 10,143,545 B2 | 12/2018 | Friedman |
| 2002/0161394 A1 | 10/2002 | Macoviak et al. |
| 2003/0004536 A1 | 1/2003 | Boylan et al. |
| 2003/0045897 A1 | 3/2003 | Huter et al. |
| 2003/0065354 A1 | 4/2003 | Boyle et al. |
| 2003/0144686 A1 | 7/2003 | Martinez et al. |
| 2003/0150821 A1 | 8/2003 | Bates et al. |
| 2004/0006366 A1 | 1/2004 | Huter et al. |
| 2004/0102834 A1 | 5/2004 | Nakano et al. |
| 2004/0167437 A1 | 8/2004 | Sharrow et al. |
| 2004/0172055 A1 | 9/2004 | Huter et al. |
| 2005/0043756 A1 | 2/2005 | Lavelle et al. |
| 2005/0288769 A1 | 12/2005 | Globerman |
| 2006/0004329 A1 | 1/2006 | Hebert et al. |
| 2006/0057183 A1 | 3/2006 | Nakano et al. |
| 2006/0125144 A1 | 6/2006 | Weber et al. |
| 2006/0129229 A1 | 6/2006 | Fukaya et al. |
| 2006/0173490 A1 | 8/2006 | Lafontaine et al. |
| 2007/0038289 A1 | 2/2007 | Nishide et al. |
| 2007/0100279 A1 | 5/2007 | Bates |
| 2007/0233183 A1 | 10/2007 | Brady et al. |
| 2007/0244503 A1 | 10/2007 | Casey et al. |
| 2008/0004690 A1 | 1/2008 | Robaina |
| 2008/0249633 A1 | 10/2008 | Wu |
| 2009/0036970 A1 | 2/2009 | Ma et al. |
| 2010/0076482 A1 | 3/2010 | Shu et al. |
| 2010/0106182 A1 | 4/2010 | Patel et al. |
| 2010/0168785 A1 | 7/2010 | Parker |
| 2010/0268264 A1 | 10/2010 | Bonnette et al. |
| 2010/0305604 A1 | 12/2010 | Pah |
| 2011/0098738 A1 | 4/2011 | Hunt |
| 2011/0137399 A1 | 6/2011 | Chomas et al. |
| 2012/0253313 A1 | 10/2012 | Galdonik et al. |
| 2013/0096606 A1 | 4/2013 | Bruchman et al. |
| 2013/0123705 A1 | 5/2013 | Holm et al. |
| 2013/0123905 A1 | 5/2013 | Abunassar et al. |
| 2013/0144328 A1 | 6/2013 | Weber et al. |
| 2013/0178891 A1 | 7/2013 | Russell et al. |
| 2013/0184742 A1 | 7/2013 | Ganesan et al. |
| 2013/0253570 A1 | 9/2013 | Bates |
| 2013/0253571 A1 | 9/2013 | Bates |
| 2013/0338761 A1 | 12/2013 | Plowiecki et al. |
| 2014/0018912 A1 | 1/2014 | Delaloye et al. |
| 2014/0031857 A1 | 1/2014 | Richardson |
| 2014/0135736 A1 | 5/2014 | Hebert |
| 2014/0236221 A1 | 8/2014 | Zhadkevich |
| 2014/0303667 A1 | 10/2014 | Cox et al. |
| 2015/0066075 A1 | 3/2015 | Russell et al. |
| 2015/0223920 A1 | 8/2015 | Bruchman et al. |
| 2016/0120636 A1 | 5/2016 | Gera et al. |
| 2016/0199169 A1 | 7/2016 | Tafti et al. |
| 2017/0000493 A1* | 1/2017 | Boehm, Jr. ...... A61B 17/12045 |
| 2017/0202657 A1 | 7/2017 | Lee et al. |
| 2018/0125683 A1 | 5/2018 | Kariniemi et al. |
| 2018/0235743 A1 | 8/2018 | Farago et al. |
| 2019/0000615 A1 | 1/2019 | Tayeb et al. |
| 2019/0015120 A1 | 1/2019 | Molaei |

FOREIGN PATENT DOCUMENTS

| | | |
|---|---|---|
| EP | 2967602 A1 | 1/2016 |
| JP | 05-130996 A | 5/1993 |
| JP | 2013-512735 A | 4/2013 |
| JP | 2014-534006 A | 12/2014 |
| WO | 99/16382 A2 | 4/1999 |
| WO | 99/32050 A1 | 7/1999 |
| WO | 02/43595 A2 | 6/2002 |
| WO | 2005/072645 A1 | 8/2005 |
| WO | 2009/068596 A1 | 6/2009 |
| WO | 2013/126618 A1 | 8/2013 |
| WO | 2014/145469 A1 | 9/2014 |
| WO | 2015/085307 A1 | 6/2015 |
| WO | 2018/183321 A1 | 10/2018 |

OTHER PUBLICATIONS

International Preliminary Report on Patentability received for PCT Patent Application No. PCT/US2018/014395, dated Aug. 1, 2019, 11 pages.

International Search Report and Written Opinion for PCT/US2012/059769 dated Apr. 19, 2013, correspondin to U.S. Appl. No. 13/448,277.

International Search Report and Written Opinion received for PCT Patent Application No. PCT/US2018/014395, dated Aug. 8, 2018, 14 pages.

International Search Report and Written Opinion received for PCT Patent Application No. PCT/US2019/056737, dated Jan. 14, 2020, 13 pages.

* cited by examiner

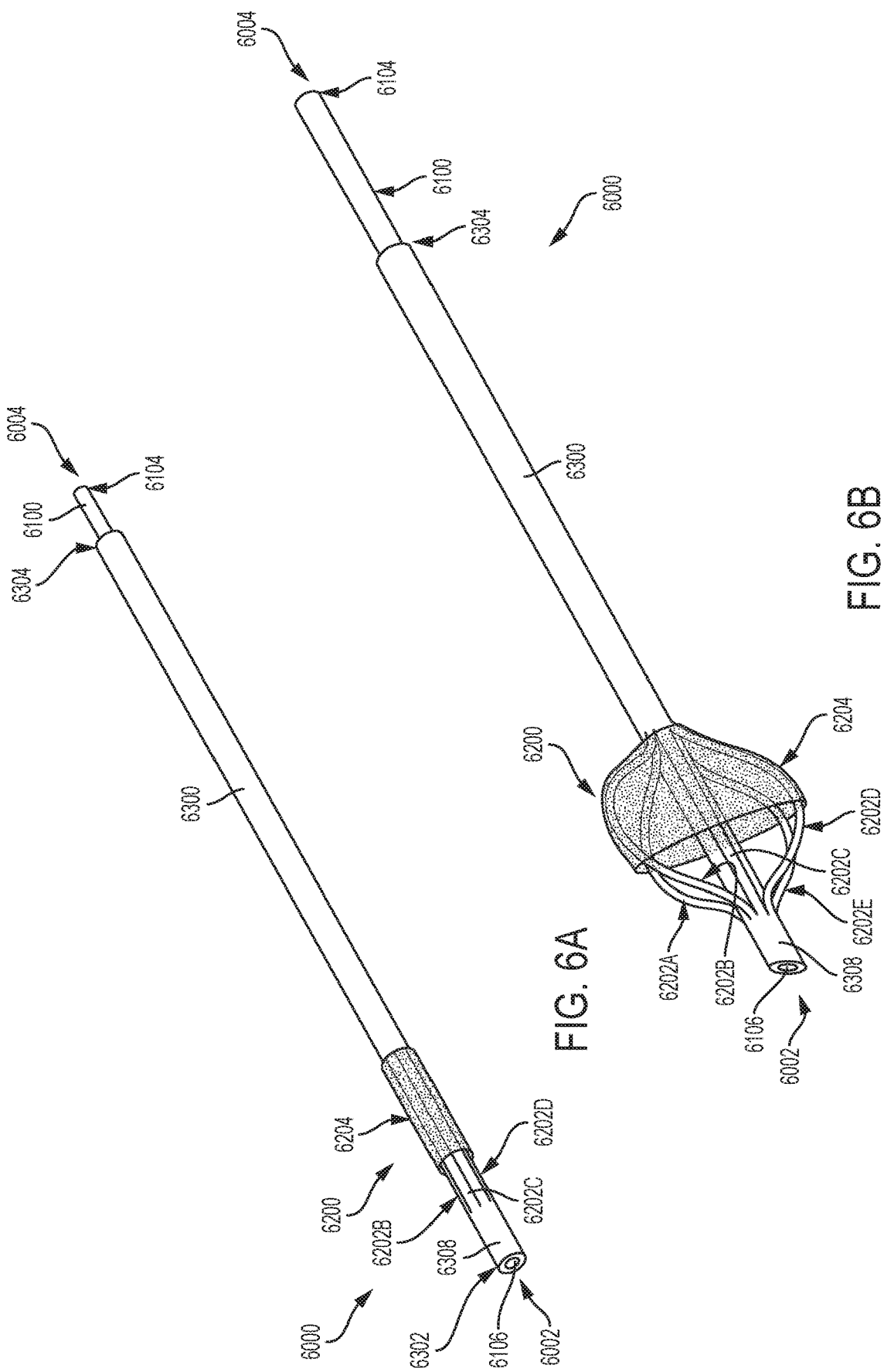

EMBOLIC FILTER SYSTEM

CROSS-REFERENCE TO RELATED APPLICATION

This application is a national phase application of PCT Application No. PCT/US2018/014395, internationally filed on Jan. 19, 2018, which claims the benefit of Provisional Application No. 62/448,802, filed Jan. 20, 2017, both of which are herein incorporated by reference in their entireties for all purposes.

BACKGROUND

Endovascular procedures address a broad array of medical needs, including endovascular access, diagnosis, and/or repair through minimally invasive or relatively less invasive means than surgical approaches. During some endovascular procedures, embolic debris may become dislodged or circulated in the vasculature. Circulation of embolic debris can cause mild to extreme cardiovascular complications, leading to stroke and even death.

Some conventional embolic protection devices used in connection with such endovascular procedures capture embolic debris in the device. For some designs, the device must be subsequently removed with the embolic debris captured therein. However, a common risk of these procedures is the unintentional release of some or all of the captured embolic debris back into the vasculature during the removal process.

Some other conventional embolic protection devices redirect the embolic debris to areas of the vasculature where its presence is associated with a lower risk of harm to the patient. Redirecting embolic debris bears with it the risk that complications may arise as a result of the redirected embolic debris migrating to another anatomical region.

SUMMARY

According to one example, ("Example 1"), an embolic filter includes an elongate element having a proximal end and a distal end, the elongate element including a first structural element and a first covering material, the elongate element having sufficient structural integrity to support being advanced within a delivery sheath, and a filter portion positioned at the distal end of the elongate element, the filter portion including a second structural element and a second covering material, wherein a portion of the second covering material includes a plurality of perforations configured to filter embolic debris from blood flowing into the filter portion.

According to another example, ("Example 2") further to Example 1, the first structure element is a self-expanding wire braid.

According to another example, ("Example 3") further to Examples 1 to 2, a distally directed force applied to the proximal end of the elongate element is operable to cause a distal translation of the elongate element and the filter portion relative to a delivery sheath.

According to another example, ("Example 4") further to Examples 1 to 3, the elongate element has sufficient structural integrity to support being advanced within a delivery sheath without requiring an introducer.

According to another example, ("Example 5") further to Examples 1 to 4, the filter portion is blood permeable and wherein the plurality of perforations have an average size of one hundred microns.

According to another example, ("Example 6") further to Examples 1 to 5, the second covering material of the filter portion is blood impermeable, and wherein plurality of perforations are formed in the second covering material such that blood is operable to flow through the second covering material of the filter portion.

According to another example, ("Example 7") further to Examples 1 to 6, the elongate element is blood impermeable.

According to another example, ("Example 8") further to Examples 1 to 7, the elongate element is configured to be advanced through a valve that operates control a flow of blood through a lumen of the elongate element during a clinical procedure.

According to another example, ("Example 9") further to Examples 1 to 8, one of the first and second covering materials include ePTFE.

According to another example, ("Example 10") an embolic filter includes a filter assembly having two ends and an elongated intermediate portion, and a structural element, wherein at a first end the filter assembly comprises an expandable filter element having an expandable frame and a filter material, and wherein the intermediate portion comprises a thin, unsupported polymer material configured to be mounted over the structural element for advancement within a catheter lumen for delivery to a treatment site, and configured to remain in place at the treatment site while the structural element is removed.

According to another example, ("Example 11") further to Example 10, the structural element is configured to advance the first end of the filter assembly from an end of the catheter for deployment at the treatment site.

According to another example, ("Example 12") further to Examples 10 to 11, the intermediate portion is configured to be advanced through a valve that operates control a flow of blood through a lumen of the intermediate portion during a clinical procedure.

According to another example, ("Example 13") further to Example 12, the lumen of the intermediate portion is configured to accommodate the advancement of one or more medical devices through the lumen of the intermediate portion during a clinical procedure, and wherein the valve is configured to control blood flow through the lumen of the intermediate portion during the clinical procedure.

According to another example, ("Example 14") further to Examples 10 to 13, the filter material is blood permeable and includes a plurality of perforations having an average size of one hundred microns.

According to another example, ("Example 15") further to Examples 10 to 14, the polymer material of the intermediate portion is blood impermeable.

According to another example, ("Example 16") further to Examples 10 to 15, one of the filter material and the polymer material include ePTFE.

According to another example, ("Example 17"), an endoprosthesis delivery device includes an expandable filter element mounted on a catheter shaft, having a capture area within the expandable filter element when the expandable filter element is deployed, and an elongated conduit configured to extend through and beyond the expandable filter element when the expandable filter element is deployed at a treatment site, the conduit configured to allow for delivery of an endoprosthesis beyond the expandable filter element, wherein the elongated conduit includes at least one aperture through a side wall providing fluid communication between the capture area and an interior of the elongated conduit.

According to another example, ("Example 18") further to Example 17, the elongated conduit extends from the catheter shaft.

According to another example, ("Example 19") further to Examples 17 to 18, the elongated conduit and the catheter shaft form a single monolithic unit.

According to another example, ("Example 20") further to Examples 17 to 19, the at least one aperture is configured to facilitate a transfer of embolic debris captured within the filter to the elongated conduit.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate examples, and together with the description serve to explain the principles of the disclosure.

FIG. 6A is an illustration of an embolic filter system consistent with various aspects of the present disclosure.

FIG. 6B is an illustration of the embolic filter system of FIG. 6B in a deployed configuration consistent with various aspects of the present disclosure.

DETAILED DESCRIPTION

Figure 1A:
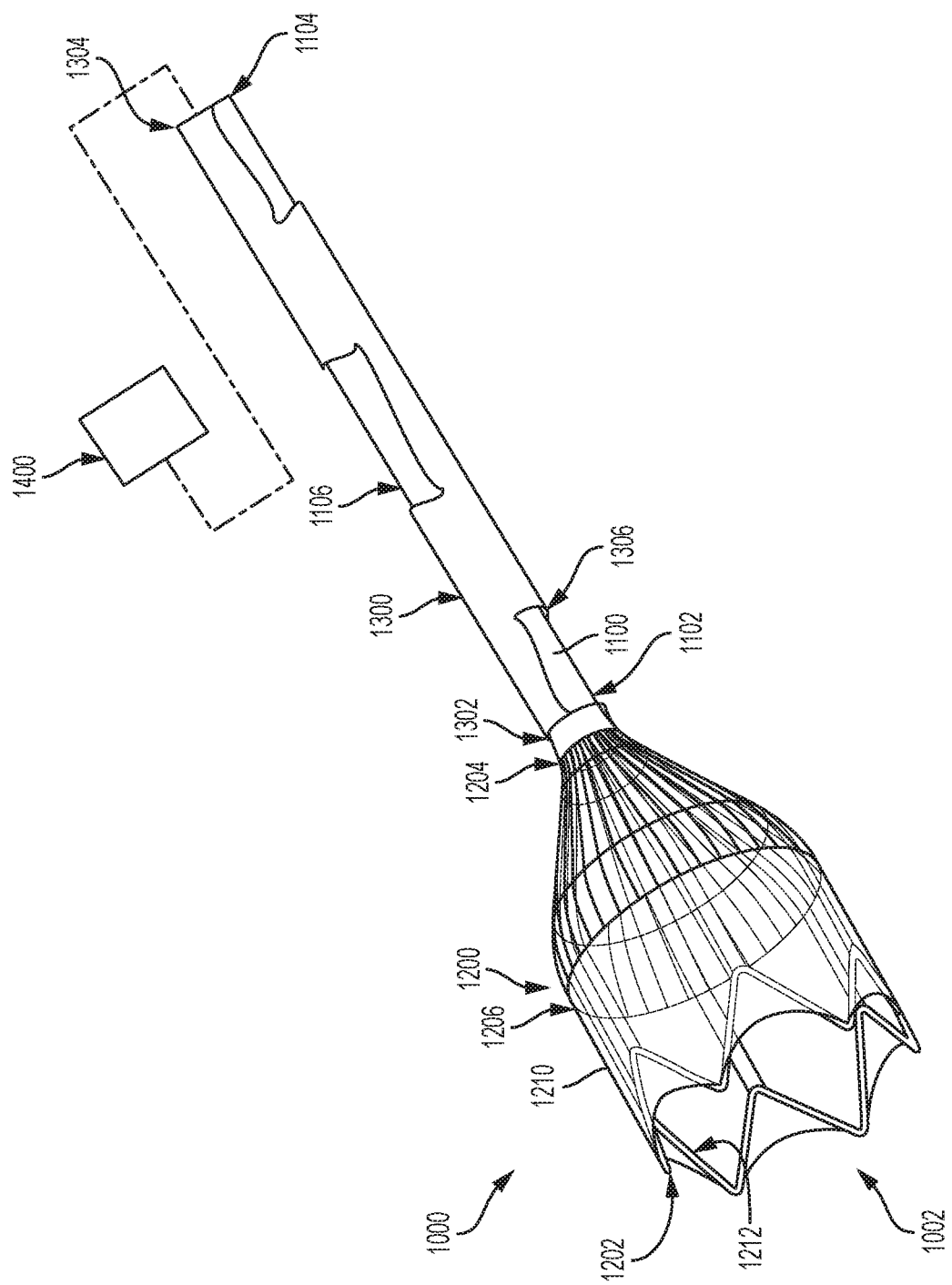
FIG. 1A is an illustration of an embolic filter system consistent with various aspects of the present disclosure.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. In describing various examples, the term distal is used to denote a position along an exemplary device proximate to or alternatively nearest to the treatment region within a patient's body. The term proximal is used to denote a position along the exemplary device proximate to or alternatively nearest to the user or operator of the device.

Various aspects of the present disclosure are directed toward an embolic filter device, system, and method. An exemplary embolic filter system 1000 is illustrated in FIG. 1A. In some examples, the embolic filter system 1000 includes a distal end 1002 and a proximal end 1004. In some examples, the distal end 1002 is situated opposite the proximal end 1004.

In various examples, the embolic filter is deployed in a region of a patient's vasculature corresponding to a treatment site. Generally, the system is advanced to a target site such that one or more components of the system (such as the filter or deflector portion) is antegrade or "downstream" of the treatment. Those of skill will appreciate that positioning the system in such a manner provides that that embolic and other debris dislodged from the treatment area during a treatment procedure will migrate with the flow of blood toward the system. The system is deployable, collapsible, and removed from the vasculature from either a distal or a proximal approach direction (e.g., antegrade or retrograde directions) to facilitate, for example, intravascular removal of the devices from different access locations.

Once deployed, the embolic filter system 1000 interacts with blood flowing through the region of the vasculature within which the embolic filter system 1000 is deployed. In some examples, embolic filter system 1000 may be adapted or otherwise configured to filter blood and/or embolic debris as it flows through or otherwise interacts with the embolic filter system 1000. In some examples, the embolic filter system 1000 additionally or alternatively redirects blood flow and/or embolic debris from what would otherwise be a normal or unimpeded flow of blood and/or embolic debris through the surrounding vasculature. Thus, in various examples, the embolic filter system 1000 can be deployed within a region of a patient's vasculature such that blood and/or embolic debris is filtered and/or redirected as it flows through that region of the patient's vasculature.

In various examples, the embolic filter system 1000 has one or more components that operate together to filter and/or redirect blood flow and embolic debris as mentioned above. For example, with reference now to FIGS. 1A and 1B, the embolic filter system 1000 includes an elongate element 1100, a filter 1200, and a constraining element 1300. It should be appreciated that various cutaways of the constraining element 1300 have been made in FIGS. 1A and 1B to illustrate portions of the elongate element 1100 otherwise obstructed from view by the constraining element 1300. In some examples, the elongate element 1100 operates as a conduit through which one or more medical devices can be delivered to a treatment site, as explained in greater detail below. In some examples, the constraining element 1300 is a catheter. In some examples, one or more components outside of the patient's body are coupled to and operate with the elongate element 1100, the filter 1200, and the constraining element 1300. For instance, one or more components 1400, such as handles, control units, and/or hemostatic valves may be coupled to the elongate element 1100, the filter 1200, and the constraining element 1300 as discussed in greater detail below. In various examples, the filter 1200 is coupled to the elongate element 1100, and the constraining element 1300 is configured to constrain the elongate element 1100 and the filter 1200 in a delivery (or collapsed) configuration.

Figure 1B:
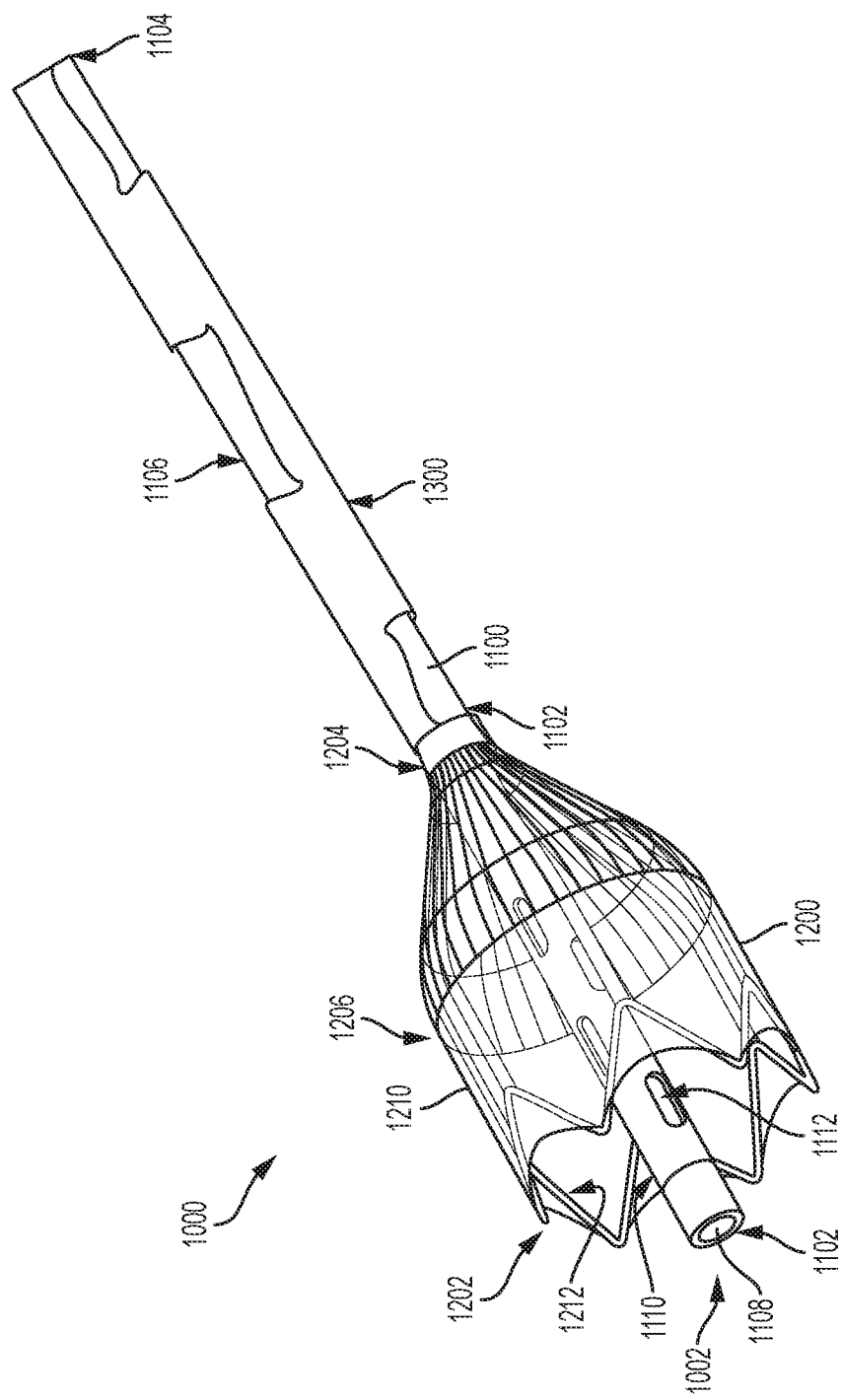
FIG. 1B is an illustration of an embolic filter system consistent with various aspects of the present disclosure.

In various examples, the elongate element 1100 is a longitudinally extending structure having a distal end 1102, a proximal end 1104, and an intermediate portion 1106 situated between the distal and proximal ends 1102 and 1104. In some examples, the elongate element 1100 is configured to receive blood and/or embolic debris. In some such examples, the elongate element 1100 filters and/or redirects blood and embolic debris flowing through the portion of the patient's vasculature within which the embolic filter system 1000 is deployed. Thus, in various examples, the elongate element 1100 includes an inner lumen, such as lumen 1108 (FIG. 1B). In some examples, blood and/or embolic debris entering the elongate element 1100 flows through the lumen 1108.

In various examples, the lumen 1108 extends through the elongate element 1100 from the distal end 1102 to the proximal end 1104. That is, in some examples, the distal and proximal ends 1102 and 1104 are open to the lumen 1108. In some examples, the lumen 1108 forms a working lumen through which one or more medical devices can be passed to treatment sites proximal to the embolic filter system 1000. Thus, in various examples, the lumen 1108 operates as both a working lumen for medical device delivery as well as a structure for redirecting and/or filtering the flow of blood and/or embolic debris.

Examples of medical devices that may be passed through the lumen 1108 include but are not limited to catheters, thrombectomy devices, atherectomy devices, embolectomy devices, and tools associated therewith, contrasting agents, drug delivery agents, endovascular prostheses including stents, stent-grafts, and valves, for example. Additionally or alternatively, the lumen 1108 is configured to house one or more release lines, steering lines, guide wires, structural support elements, and/or introducers, and related components as will be explained further below.

In various examples, the filter 1200 is a structure configured to interact with blood and/or embolic debris flowing through the patient's vasculature in the region within which the embolic filter system 1000 is deployed. In some examples, the filter 1200 is configured to direct or funnel blood and embolic debris such that the blood and embolic debris enter the filter 1200 and, in some examples, the elongate element 1100.

In various examples, the filter 1200 includes a distal end 1202, a proximal end 1204, and an intermediate portion 1206. As shown in FIGS. 1A and 1B, in some examples, the filter 1200 includes a membrane 1210 and a structural support 1212. The structural support 1212 may be formed of nitinol or other suitable materials and may be laser cut, braided, or wire-wound. In some examples, the structural support 1212 is formed of a laser cut nitinol tube, as those of skill will appreciate.

In some examples, the membrane 1210 is disposed about the structural support 1212. In some examples, the structural support 1212 is disposed about the membrane 1210. In various examples, the structural support 1212 provides structural support to the membrane 1210. In some examples, as discussed in greater detail below, the filter 1200 is self-expanding and/or radially collapsible. The filter 1200 may be of any suitable size for endovascular delivery and deployment.

In some examples, both the distal and proximal ends 1202 and 1204 of the filter 1200 are open such that the flow of blood can enter the filter 1200 at the distal end 1202 and exit the filter 1200 at the proximal end 1204. Thus, in some examples, the membrane 1210 is configured such that the filter 1200 has a lumen extending therethrough. Generally, this lumen operates as an area for capturing blood and embolic debris. In some examples, the proximal end 1204 of the filter 1200 is coupled to the elongate element 1100 such that the blood exiting the proximal end 1204 of the filter 1200 enters or otherwise interacts with the elongate element 1100.

In such examples, the coupling between the elongate element 1100 and the filter 1200 can be permanent or temporary. In some examples, the elongate element 1100 is coupled to the filter 1200 such that the elongate element 1100 and the filter 1200 form a single monolithic unit. In some other examples, the filter 1200 is removable from the elongate element 1100. In some examples, the filter 1200 is slidable relative to the elongate element 1100.

In some examples, the filter 1200 is coupled or otherwise secured at or proximate to an end of the elongate element 1100, such as a distal end 1102 of the elongate element 1100. For example, the embolic filter system 1000 illustrated in FIG. 1A includes a filter 1200 coupled at a distal end 1102 of the elongate element 1100.

In some other examples, however, the filter 1200 is coupled to the elongate element 1100 at some position along the elongate element 1100 proximal to the distal end 1102 of the elongate element 1100. For example, the illustrated embolic filter system 1000 illustrated in FIG. 1B includes a filter 1200 that is coupled to the elongate element 1100 at a position along the elongate element 1100 proximal of the distal end 1102 of the elongate element 1100. In some such examples, the filter 1200 is coupled to the elongate element 1100 such that a distal end 1202 of the filter 1200 is situated proximal of the distal end 1102 of the elongate element 1100. Thus, in some examples, the distal end 1102 of the elongate element 1100 extends distal to the distal end 1202 of the filter 1200 and thus corresponds with or otherwise defines a distal end 1002 of the embolic filter system 1000. As explained in greater detail below, such a distally projecting portion of the elongate element 1100 protects against entanglement between the filter 1200 and the medical devices being delivered to the treatment site through the lumen 1108.

It will be appreciated, that in some examples, the filter 1200 is coupled to the elongate element 1100 such that the distal end 1102 of the elongate element 1100 is situated between the distal end 1202 and a proximal end 1204 of the filter 1200. That is, although the filter 1200 is coupled to the elongate element 1100 at a position along the elongate element 1100 proximal to the distal end 1102 of the elongate element 1100, the distal end 1202 of the filter 1200 corresponds with or otherwise defines a distal end 1002 of the embolic filter system 1000 (i.e., the distal end 1202 of the filter 1200 is positioned distal to the distal end 1102 of the elongate element 1100). In some other examples, the filter 1200 is coupled to the elongate element 1100 such that the distal end 1102 of the elongate element 1100 and the distal end 1202 the filter 1200 are positioned equally distal relative to one another. In other words, the distal end 1102 of the elongate element 1100 is not (or is not substantially) positioned distal the distal end 1202 of the filter 1200 and vice versa.

In some examples, a proximal end of the filter is coupled to a distal end a first elongate element, and a second elongate element is coupled to the filter and/or the first elongate element such that the second elongate element extends within or through an interior region of the filter distal the first elongate element. In some examples, similar to the discussion above, the distal end of the second elongate element is positioned distal to, at, or proximal to the distal end of the filter.

In some examples, the filter 1200 deflects or otherwise redirects blood and/or embolic debris such that the blood and/or embolic debris flows into the filter 1200. In some examples, the filter 1200 operates to filter or otherwise condition the blood and embolic debris flowing therethrough. In some examples, the filter 1200 is permeable to certain blood media (e.g., blood-permeable) and impermeable to certain other blood media and/or embolic debris. Specifically, in some examples, the membrane 1210 of the filter 1200 is configured such that certain blood media (e.g., red blood cells, white blood cells, plasma, platelets, etc.) flowing through the filter 1200 can permeate the membrane 1210 of the filter 1200 and re-enter the vasculature while the filter 1200 is impermeable to certain other blood media and embolic debris. In some examples, the filter 1200 is impermeable to embolic debris of a designated size or larger. That is, in some examples, the membrane 1210 of the filter 1200 operates to obstruct embolic debris of a designated size or larger from permeating the membrane 1210 of the filter 1200 and re-entering the vasculature.

In some examples, the blood media and embolic debris flowing through the filter 1200 that does not permeate back into the vasculature is either captured and retained within the filter 1200 or is further directed into the elongate element 1100. In some examples, as explained in greater detail below, the filter 1200 is collapsible such that the blood media and embolic debris that is retained within the filter 1200 can be subsequently removed from the patient's body.

As mentioned above, in some examples, some or all of the blood and/or embolic debris flowing into the filter 1200 is further directed into the elongate element 1100. In some examples, the blood and/or embolic debris that is directed into the elongate element 1100 enters the lumen 1108 of the elongate element 1100. In some examples, as explained in greater detail below, the filter 1200 is configured to filter the blood and/or embolic debris entering the inner lumen 1108. Thus, in some examples, the elongate element 1100 is configured to filter the blood and/or embolic debris that did not permeate through the filter 1200.

As mentioned above, in some examples, the filter 1200 and/or the elongate element 1100 operate to filter embolic debris from a patient's blood flowing through the embolic filter system 1000. Generally, the permeability of the elongate element 1100 and/or the membrane 1210 can be controlled by manipulating one or more of the material properties of the material of which the elongate element 1100 and/or the membrane 1210 is comprised. For example, a node and fibril configuration of an expanded fluoropolymer can be optimized based on the desired permeability. In some examples, an expanded fluoropolymer can be processed such that a node and fibril configuration of the expanded fluoropolymer is generally impermeable to embolic debris (and other blood media) of a designated size.

It will thus be appreciated that the elongate element 1100 and the filter 1200 can comprise various materials including, but not limited to polymers such as fluoropolymers like an expanded polytetrafluoroethylene ("ePTFE"), expanded PTFE, expanded modified PTFE, expanded copolymers of PTFE, nylons, polycarbonates, polyethylenes, polypropylenes and the like.

In various examples, one or more regions of a material may be further or alternatively modified by forming one or more perforations therein. For example, a material such as an expanded fluoropolymer (or another suitable polymer) can be further modified by perforating one or more regions of the material to achieve a designated porosity in those regions. Examples include laser cutting holes or perforations into a material. Other materials having a woven, knitted or lattice configuration may also serve as adequate materials based on their permeability/porosity.

Additionally, in some examples, a material can be configured such that one or more portions or regions of the elongate element 1100 and/or the membrane 1210 of the filter 1200 are permeable to a media up to a designated size while one or more other portions or regions of the elongate element 1100 and/or the membrane 1210 are impermeable to the media. In some examples, the elongate element 1100 and/or the filter 1200 can have a variable pore or perforation size, for example, from a proximal end to a distal end and/or at one or more discrete locations (e.g., such as at one or more of the permeable windows discussed below). For example, a distal region of the elongate element 1100 and/or the filter 1200 can have a smaller average perforation size to avoid smaller embolic debris entering the great vessels, whereas a more proximal region of the elongate element 1100 and/or the filter 1200 can have a larger average perforation size beyond a point where entry of the smaller embolic debris into the great vessels is not a concern.

In some examples, varying permeability may be achieved by varying a number of layers of a material along the elongate element 1100 and/or the filter 1200. For example, a first region of a material having a first number of layers of an expanded fluoropolymer is associated with a first degree of permeability while a second region of the material having a second number of layers of an expanded fluoropolymer is associated with a second degree of permeability. In some such examples, the permeability of a region of such a material is inversely related to the number of layers of the expanded fluoropolymer integrated into the material in that region.

In some other examples, a varying degree of permeability can be achieved by alternatively or additionally varying a diameter or area of each of the perforations or the perforation density made in one region of the material relative to another region of the material. In one such example, a first area or region (e.g., distal) may be associated with one or more perforations having a first average perforation size and a second area or region (e.g., proximal) may be associated with one or more perforations having a second average perforation size. Thus, in various examples, the filter 1200 and/or the elongate element 1100 may include areas or regions with variable pore sizes. It will be appreciated that by varying the pore size or permeability, the filtration of embolic debris along the embolic filter system 1000 can be controlled and the risk of potentially harmful embolic debris perfusing into critical areas can be minimized.

In various examples, the perforations or pore sizes discussed above may be selected such that a region or area of the elongate element 1100 and/or the membrane 1210 of the filter 1200 is impermeable to embolic debris greater than or equal to about 100 μm. In such examples, it will be appreciated that the average pore size in such areas is less than 100 μm. However, in other examples, the pore sizes may be selected such that a region or area of the material is impermeable to embolic debris smaller than 100 μm, such as embolic debris in the range of 40 μm to 99 μm. In yet other examples, other regions or areas of the material may be permeable to embolic debris greater than 100 μm, such as embolic debris in the range of 101 μm to 150 μm. It will be appreciated that the average pore size in such areas is greater than or equal to 101 µm to 150 µm.

Referring still to FIGS. 1A and 1B, in various examples, the filter 1200 is expandable such that the filter 1200 occupies the area (or a substantial portion of the area) of the vessel within which it is deployed. In various examples, the filter 1200 is expanded once it is advanced to a target site at or proximate to a treatment area. Thus, in various examples, a filter 1200 is transitionable between a radially collapsed delivery configuration and a radially expanded deployed configuration. In some examples, the filter 1200 is self-expanding. In some examples, one or more expandable elements are utilized to transition the filter 1200 between the radially collapsed delivery configuration and the radially expanded deployed configuration. For example, a balloon may be utilized to transition the filter 1200 to the radially expanded deployed configuration from the radially collapsed delivery configuration.

In the deployed configuration, the filter 1200 adopts a generally trumpeted, conical, or frustoconical shape in that a transverse cross-sectional area of the filter 1200 is different at two different locations along the filter 1200 between the distal and proximal ends 1202 and 1204 of the filter 1200. In one such example, the transverse cross-sectional area of the distal end 1202 is greater than the transverse cross-sectional area of the proximal end 1204. In some examples, the filter 1200 generally tapers from the distal end 1202 to the proximal end 1204. Such a configuration provides that the filter 1200 operates to funnel the blood into the filter 1200 and/or into the elongate element 1100 as disclosed herein.

In some examples, one or more constraining members, such as constraining element 1300, operate to maintain the filter 1200 and/or a portion thereof in the radially collapsed delivery configuration. In some examples, the constraining element 1300 is releasable or removable such that the filter 1200 is transitionable to the radially expanded deployed configuration.

Generally, depending on the desired configuration, the constraining element 1300 can comprise various materials including, but not limited to polymers, such as fluoropolymers like an expanded polytetrafluoroethylene ("ePTFE"), expanded PTFE, expanded modified PTFE, expanded copolymers of PTFE, nylons, polycarbonates, polyethylenes, polypropylenes and the like. Thus, in some examples, the constraining element 1300 can advanced or retracted relative to the filter 1200.

Referring still to FIGS. 1A and 1B, in various examples, the embolic filter system 1000 includes a constraining element 1300. In some examples, the constraining element 1300 is an elongated member having a distal end 1302 and a proximal end 1304. In some examples, the constraining element 1300 is cylindrical, however, constraining elements having oblong cross sections are also envisioned. In various examples, an interior lumen 1306 extends through the constraining element 1300 from the distal end 1302 to the proximal end 1304. In some examples, as mentioned above, the interior lumen 1306 is configured to receive the elongate element 1100 therein. Thus, in some such examples, the elongate element 1100 and the constraining element 1300 are coaxial. Likewise, in various examples, a portion of or all of the filter 1200 is received within the constraining element 1300 such that the filter 1200 is maintained in a radially collapsed delivery configuration.

In various examples, the elongate element 1100 is received within the constraining element 1300 such that the elongate element 1100 and the constraining element 1300 can be moved relative to one another. As explained in greater detail below, moving the elongate element 1100 and the constraining element 1300 relative to one another facilitates both the deployment and the collapsing of the filter 1200.

In some examples, the constraining element 1300 is retractable such that the distal end 1302 of the constraining element 1300 translates proximally away from the distal end 1202 of the filter 1200. In some such examples, the elongate element 1100 and/or the filter 1200 are held fixed while the constraining element 1300 is retracted. In other examples, the elongate element 1100 and/or the filter 1200 are advanced while the constraining element 1300 is retracted. In some examples, the elongate element 1100 and/or the filter 1200 are advanced relative to the constraining element 1300 such that the filter 1200 moves distally away from the proximal end 1304 of the constraining element 1300. In some examples, the constraining element 1300 is held fixed while the elongate element 1100 and/or the filter is advanced. In other examples, the constraining element 1300 is retracted while the elongate element 1100 and/or the filter is advanced.

In various examples, the advancement of the filter 1200 distally away from the distal end 1302 of the constraining element 1300 facilities deployment of the filter 1200. That is, the filter 1200 can be transitioned from the radially collapsed delivery configuration to the radially expanded deployed configuration by advancing the filter 1200 distally away from the distal end 1302 of the constraining element 1300 and/or retracting the distal end 1302 of the constraining element 1300 away from the distal end 1202 of the filter 1200.

As mentioned above, in some examples, the filter 1200 can be transitioned from the radially expanded deployed configuration to the radially collapsed delivery configuration. In some examples, with the filter 1200 transitioned to the radially collapsed delivery configuration, the embolic filter system 1000 can be withdrawn from the patient's vasculature. In some examples, a deployed filter 1200 is transitioned to the radially collapsed delivery configuration by advancing the constraining element 1300 toward the distal end 1202 of the filter 1200 until the filter 1200 is radially collapsed and retained by the constraining element 1300, as discussed in greater detail below. Alternatively or additionally, the filter 1200 can be withdrawn proximally relative to the constraining element 1300.

As discussed above, in various examples, the filter 1200 is coupled to the elongate element 1100 at a position along the elongate element 1100 proximal to the distal end 1102 of the elongate element 1100 such that a distal end 1102 of the elongate element 1100 is positioned distal to the proximal end 1204 of the filter 1200. With specific reference to FIG. 1B, an exemplary embolic filter system 1000 includes an elongate element 1100 having a distal end 1102 that is positioned distal to a proximal end 1204 of the filter 1200 such that a distal portion 1110 of the elongate element 1100 extends distally beyond the proximal end 1204 of the filter 1200. As mentioned above, in various examples, the elongate element 1100 includes an inner lumen 1108 through which one or more medical devices can be delivered to a treatment site located distally of the distal end 1002 of the embolic filter system 1000.

In some examples, the distal portion 1110 provides that such medical devices can be delivered with a decreased risk that such medical devices will become entangled with the filter 1200. In other words, the portion (distal portion 1110) of the elongate element 1100 that extends distal to the proximal end 1204 of the filter 1200 operates as a barrier between the medical device being delivered and the filter 1200. Accordingly, such a configuration is associated with a decreased risk that the delivered medical device will interfere with the filter 1200 as the delivered medical device exits the distal end 1102 of the elongate element 1100. Those of skill in the art will appreciate that such a configuration helps minimize a risk of tearing or otherwise damaging of the filter 1200 as a result of a medical device entangling with the filter 1200.

In addition to protecting against entanglement between the filter 1200 and a delivered medical device, in some examples, the distal portion 1110 of the elongate element 1100 operates to capture embolic material trapped in the filter 1200 as the filter is radially collapsed for removal of the embolic filter system 1000. Specifically, in some examples, the distal portion 1110 includes one or more apertures 1112 that extend from an exterior surface 1114 of the distal portion 1110 to the inner lumen 1108 of the elongate element 1100. Accordingly, the one or more apertures 1112 provide a pathway for embolic debris captured by the filter 1200 to enter the lumen 1108. In some examples, such a configuration additionally or alternatively facilitates the aspiration of the embolic debris from the embolic filter system 1000. In some such examples, aspiration of the embolic debris can be achieved before or after radially collapsing the filter 1200 and/or withdrawing the embolic filter system 1000 from the patient's vasculature. Those of skill will appreciate that by providing a mechanism for evacuating embolic debris that is otherwise captured within the filter 1200, the embolic filter system 1000 helps minimize the risk that the captured embolic debris will be accidentally released back into the patient's vasculature during removal of the embolic filter system 1000 from the patient's vasculature.

For example, a known risk during embolic debris filtering procedures is the risk of tearing the filter (or filter material) during removal. Generally, embolic filters filled with embolic debris generally occupy a larger cross sectional area than do embolic filters free of embolic debris. This increased cross section can be associated with difficultly in sufficiently collapsing the embolic filter to a configuration wherein the embolic filter can be completely retracted within a constraining sheath. Even where the filter is not retracted within a constraining sheath, withdrawing a filter having a larger diameter as a result of being filled with embolic debris through tortuous vasculature can be difficult. Providing a mechanism that enables the evacuation of some or all of the embolic debris from the filter helps minimize the above-discussed risks.

In some examples, a cross sectional area of the distal portion 1110 of the elongate element 1100 is less than a cross sectional area of the portion of the elongate element 1100 situated proximal of the proximal end 1204 of the filter 1200. In some such examples, the distal portion 1110 of the elongate element 1100 has an outside diameter that is less than an outside diameter of the portion of the elongate element 1100 situated proximal of the proximal end 1204 of the filter 1200. In one such example, however, an inside diameter of the distal portion 1110 is the same as (or substantially the same as) an inside diameter of the portion of the elongate element 1100 situated proximal of the proximal end 1204 of the filter 1200. In other words, although a cross section area (or an outside diameter) of the distal portion 1110 is less than that of the portion of the elongate element 1100 situated proximal of the proximal end 1204 of the filter 1200, a diameter or cross sectional area of the inner lumen 1108 is generally constant between the distal and proximal ends 1102 and 1104 of the elongate element 1100. Thus, in some examples, it will be appreciated that the elongate element 1100 has a varying wall thickness along its length.

Put differently, in some examples, the distal portion 1110 has a first inner diameter and a first outer diameter, and the portion of the elongate element 1100 situated proximal of the proximal end 1204 of the filter 1200 has the first inner diameter and a second outer diameter, wherein the second outer diameter is greater than the first outer diameter.

Figure 2:
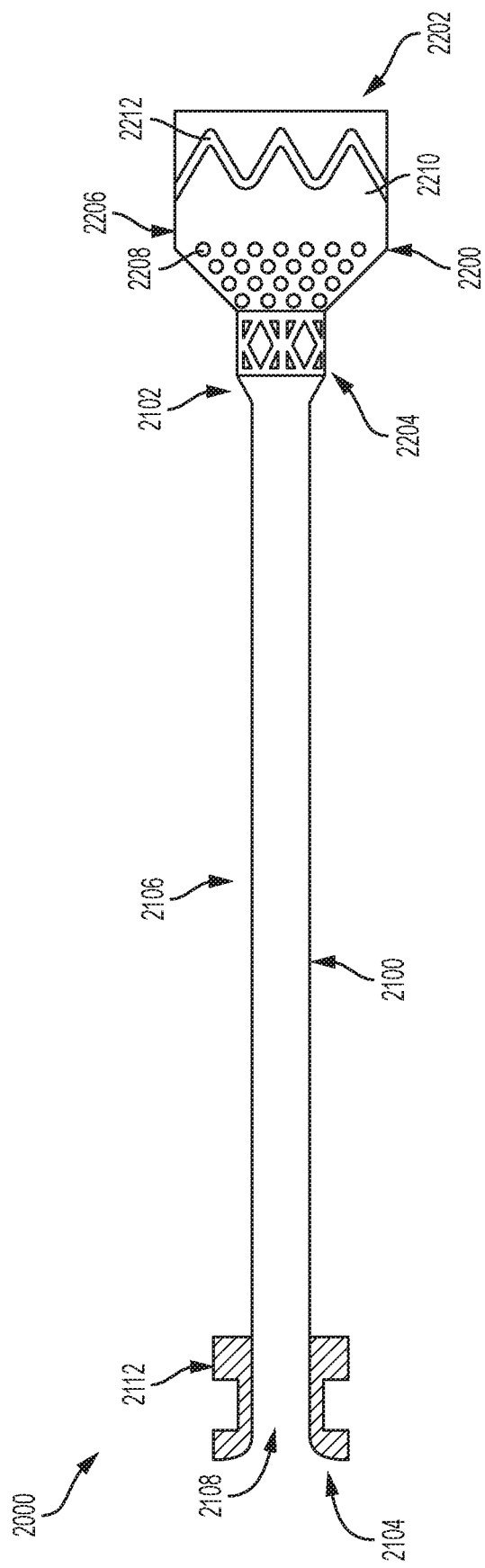
FIG. 2 is an illustration of an embolic filter system consistent with various aspects of the present disclosure.
Figure 3:
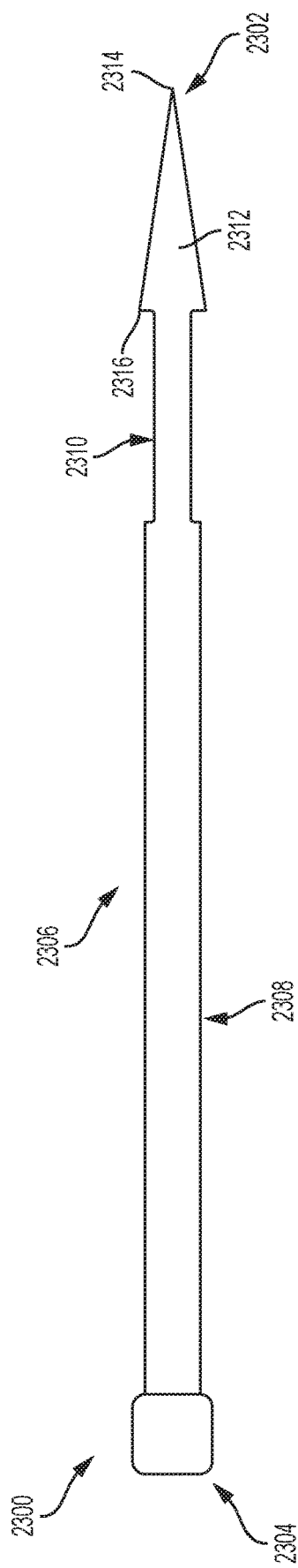
FIG. 3 is an illustration of an introducer consistent with various aspects of the present disclosure.

Turning now to FIGS. 2 and 3, various components of an embolic filter system 2000 are illustrated. As shown, the embolic filter system 2000 includes an elongate element 2100, a filter 2200 (similar to filter 1200), and an introducer 2300. As shown in FIG. 4, in some examples, the embolic filter system 2000 further includes a constraining member 2400 (similar to constraining element 1300) and a hemostatic sealing member 2500.

Similar to the elongate element 1100, in various examples, the elongate element 2100 can comprise various materials including, but not limited to polymers, such as fluoropolymers like an expanded polytetrafluoroethylene ("ePTFE"), expanded PTFE, expanded modified PTFE, expanded copolymers of PTFE, nylons, polycarbonates, polyethylenes, polypropylenes and the like. Similar to elongate element 1100, elongate element 2100 extends longitudinally and includes a distal end 2102, a proximal end 2104, and an intermediate portion 2106 situated between the distal and proximal ends 2102 and 2104. In some examples, the elongate element 2100 is configured to receive blood and/or embolic debris. In some such examples, the elongate element 2100 filters and/or redirects blood and embolic debris flowing through the portion of the patient's vasculature within which the embolic filter system 2000 is deployed. Thus, in various examples, the elongate element 2100 includes an interior lumen, such as lumen 2108 (FIG. 2).

In various examples, the lumen 2108 extends through the elongate element 2100 from the distal end 2102 to the proximal end 2104. That is, in some examples, the distal and proximal ends 2102 and 2104 are open to the lumen 2108. In some examples, the lumen 2108 forms a working lumen through which one or more medical devices can be passed to a treatments site proximal of the embolic filter system 2000, as explained above.

In some examples, the elongate element 2100 is formed of a material, such as an expanded fluoropolymer like ePTFE. Accordingly, in some examples, the elongate element 2100 is a soft and compliant material. In some examples, the elongate element 2100 lacks sufficient structural rigidity to support its own weight and has little to no column strength when subjected to a longitudinal compressive force. Likewise, in some such examples, the elongate element 2100 is not generally torqueable in that the elongate element will not generally transfer a torque applied to its first end to its second end. However, as those of skill in the art will appreciate, an elongate element 2100 made of an expanded fluoropolymer exhibits good tensile strength in that a longitudinal tensile force applied to a first end of the elongate element 2100 is generally transferred along the elongate element 2100.

Elongate elements formed of a fluoropolymer like ePTFE have an added advantage over other materials and designs in that an elongate element formed of a fluoropolymer like ePTFE can have a working lumen with a diameter larger than the diameters of conventional designs without increasing the outside working diameter of the system. In other words, elongate elements formed of a fluoropolymer like ePTFE can be configured with thin or very thin walls (e.g., a range of between 0.0001 and 0.010 inches) to maximize the inner diameter of the working lumen without impacting the overall size of the device. For instance, in some examples, elongate elements formed of a fluoropolymer like ePTFE can be configured with and average wall thickness of approximately 0.001 inches. It should be appreciated that the high tensile strength of a fluoropolymer like ePTFE enables a configuration having thin walls which maximizes the area of the working lumen (as further discussed herein).

In some examples, like the elongate element 1100, the elongate element 2100 may be blood-permeable while remaining impermeable to embolic debris and other blood media in excess of a particular size or cross section. Likewise, similar to elongate element 1100, the elongate element 2100 may include one or more perforations and/or a varying permeability or porosity along its length.

In some examples, as explained in greater detail below, the elongate element 2100 includes a stopping feature 2112 (FIG. 2). In some examples, the stopping feature 2112 is integral to the elongate element 2100. In other examples, the stopping feature 2112 is a separate component that is coupled to the elongate element 2100. In some examples, the stopping feature 2112 is positioned at or near the proximal end 2104 of the elongate element 2100. In some examples, the stopping feature 2112 operates to control how far into the vasculature the elongate element 2100 may be advanced. In some examples, the stopping feature 2112 additionally or alternatively operates as a pulling feature for withdrawing the elongate element 2100 and the filter 2200 from the vasculature. Thus, in some examples, the stopping feature 2112 operates as a capture feature that facilitates capturing and withdrawing the elongate element 2100 and the filter 2200 from the vasculature. In some examples, the stopping feature 2112 is a rigid or semi-rigid and may be formed of a polymer such as polypropylene, polyethylene, polyamides, polyetheretherketone, or other suitable plastic for example.

In various examples, like the filter 1200, the filter 2200 is a structure configured to interact with blood and/or embolic debris flowing through the patient's vasculature in the region within which the embolic filter device 2000 is deployed. In various examples, the filter 2200 includes a distal end 2202, a proximal end 2204, and an intermediate portion 2206. Likewise, in some examples, the filter 2200 includes a membrane 2210 and a structural support 2212. Thus, in some examples, like the filter 1200, the filter 2200 is self-expanding and/or radially collapsible.

In some examples, both the distal and proximal ends 2202 and 2204 of the filter 2200 are open such that the flow of blood can enter the filter at the distal end 2202 and exit the filter at the proximal end 2204. In some examples, the proximal end 2204 of the filter 2200 is coupled to the elongate element 2100 such the blood exiting the proximal end 2204 of the filter 2200 enters or otherwise interacts with the elongate element 2100. In such examples, as explained above with regard to elongate element 1100, the coupling between the elongate element 2100 and the filter 2200 can be permanent or temporary.

Additionally, like the filter 1200, in some examples, the filter 2200 operates to filter or otherwise condition the blood and embolic debris flowing therethrough. Thus, in some examples, the filter 2200 is permeable to certain blood media (e.g., blood-permeable) and impermeable to certain other blood media and/or embolic debris (e.g., embolic debris and blood media of a designated size or larger). Likewise, one or more regions may be permeable while one or more other regions may be impermeable (or less permeable as discussed herein). In some examples, as explained in greater detail below, the filter 2200 is collapsible such that the blood media and embolic debris that is retained within the filter 2200 can be subsequently removed from the patient's body.

As mentioned above, the permeability/porosity of an elongate element or filter, like elongate element 2100 and/or filter 2200 can be controlled by manipulating one or more of the material properties of the material of which the elongate element and/or filter is comprised (e.g., node and fibril configuration, perforation, weave, knit, and lattice configurations).

As show in FIG. 2, the filter 2200 includes a plurality of perforations 2208. In some examples, these perforations 2208 are configured to filter embolic debris from the patient's blood. For instance, the perforations 2208 may be between 50 microns and 1000 microns, and thus may be operable to filter debris as little as 50 microns. While the perforations are illustrated as being generally circular in geometry, it will be appreciate that other shapes, such as polygonal geometries, are envisioned and may be utilized in addition to or in lieu of circular geometries without departing from the spirit or scope of the disclosure. As explained above, perforations 2208 (and/or node and fibril configurations, and/or weaves, and/or knits, and/or lattice configurations, and/or layering, etc) can vary across a material (e.g., from a proximal end to a distal end and/or at one or more discrete locations). Additionally, while the filter 2200 illustrated in FIG. 2 show perforations along only a portion thereof, it should be appreciated that perforations may be included at any and all surfaces of the filter 2200.

Turning now to FIG. 3, in various examples, the introducer 2300 is a longitudinally extending structure configured to facilitate delivery of the embolic filter system to a treatment site within a patient's vasculature (or to a location proximal thereto). Specifically, in some examples, the introducer 2300 is configured such that the elongate element 2100 and the filter 2200 can be loaded onto the introducer and delivered to the treatment site within the patient's vasculature. As shown, an exemplary introducer 2300 includes a distal end 2302 and a proximal end 2304. In some examples, an intermediate portion 2306 is situated between the distal end and the proximal end 2302 and 2304. In some examples, the introducer 2300 includes an elongate element mounting portion 2308 and a filter mounting portion 2310. In some examples, the intermediate portion 2306 includes the elongate element mounting portion 2308 and the filter mounting portion 2310.

In some examples, the introducer 2300 is generally cylindrically shaped, however, other profiles are envisioned. In addition, in some examples, the introducer 2300 may have any suitable cross sectional profile including, but not limited to, circular and oblong cross sections. In some examples, the introducer 2300 includes a blunt tip at its distal end 2302. In some examples, the proximal end 2304 includes a tip that generally tapers. For example, as show in FIGS. 4A and 4B, the introducer 2300 includes a tapered tip 2312 having a distal end 2314 with a smaller cross section than a proximal end 2316. In some examples, the distal end 2314 of the tapered tip 2312 corresponds to the distal end 2304 of the introducer 2300. In some examples, the tapered tip 2312 extends from the filter mounting portion 2310 and is positioned distally thereof.

As mentioned above, the introducer 2300 is configured to facilitate delivery of the elongate element 2100 and the filter 2200 to the treatment site (or a position proximal thereto) such that the elongate element 2100 and the filter 2200 can operate to filter embolic debris from the patient's blood.

Those of skill in the art will appreciate that due to its soft and compliant nature, the elongate element 2100 cannot be easily advanced through the vasculature without the assistance of the introducer 2300. In short, if the elongate element 2100 is not mounted on the introducer 2300, applying a distally directed force to the proximal end 2104 of the elongate element 2100 will have little, if any effect, on translating the distal end of the elongate element 2100. Under such circumstances, as those of skill in the art will appreciate, the elongate element 2100 will buckle (or accordion) along its longitudinal length. Accordingly, for soft and compliant elongate elements like elongate element 2100, an introducer 2300 is utilized to advance the elongate element (and thus the filter 2200) through the patient's vasculature to the target site.

In some examples, the elongate element mounting portion 2308 of the introducer 2300 is complementary of the elongate element 2100 (e.g., length, shape, cross sectional area etc) such that the elongate element 2100 can be mounted thereon. In some examples, the elongate element mounting portion 2308 is a smooth continuous surface. In some such examples, when mounted on the introducer 2300, the elongate element 2100 is supported by the elongate element mounting portion 2308 of the introducer 2300.

Likewise, in some examples, the filter mounting portion 2310 of the introducer 2300 is complementary of the filter 2200 (e.g., length, shape, cross sectional area etc) when the filter 2200 is radially collapsed and configured for delivery. In some examples, the filter mounting portion 2310 is formed as a relief in the introducer 2300. In some examples, the relief is a circumferential relief, though it need not be. In some examples, a removable constraining sheath is disposed about at least the filter and/or elongate element to maintain the filter and/or the elongate element in the delivery configuration on the introducer as will be appreciated by those of skill in the art. In such examples, the constraining sheath can be removed upon delivery of the elongate element and the filter to the target site, wherein the filter can expand to its radially expanded deployed configuration. In various examples, the removable constraining sheath may be a sleeve, sheath, sock or other constraining mechanism. Those of skill in the art will appreciate that deployment of the filter can occur proximal to distal, distal to proximal, ends inward, center outward, etc.

In some examples, when the filter 2200 is radially collapsed and mounted thereon, the radially collapsed filter 2200 is received within the relief. For instance, the relief has a radial depth sufficient to accommodate the membrane and/or structural elements of the filter such that the radially collapsed filter does not project radially beyond the elongate element disposed about (or mounted on) the elongate element mounting portion 2308. Such a configuration provides for a system having a minimal delivery profile.

In some examples, a position of the elongate element and the filter along the introducer is maintained during delivery as a result of the radially collapsed filter being received within the circumferential relief. Specifically, as will be appreciated by those of skill in the art, when the filter is radially collapsed and received by the filter mounting portion, force applied to the introducer is transferred to the filter by the relief. Thus, with the filter radially collapsed and received by the filter mounting portion, translational motion of the introducer is transferred to the filter such that the filter and the elongate element translate with the introducer.

Figure 4A:
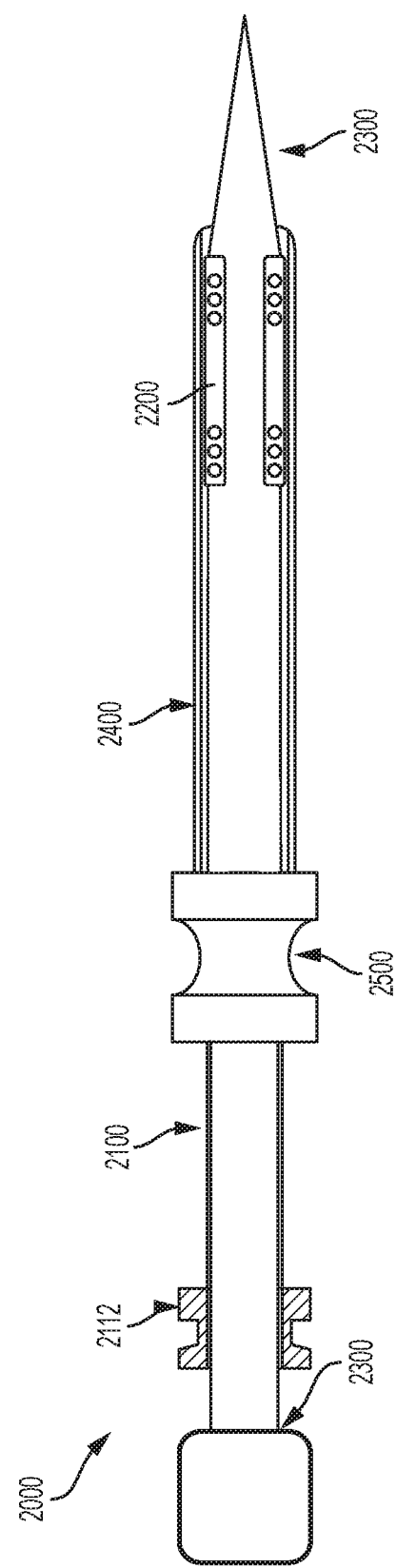
FIGS. 4A-4C are illustrations of an embolic filter system consistent with various aspects of the present disclosure.
Figure 4B:
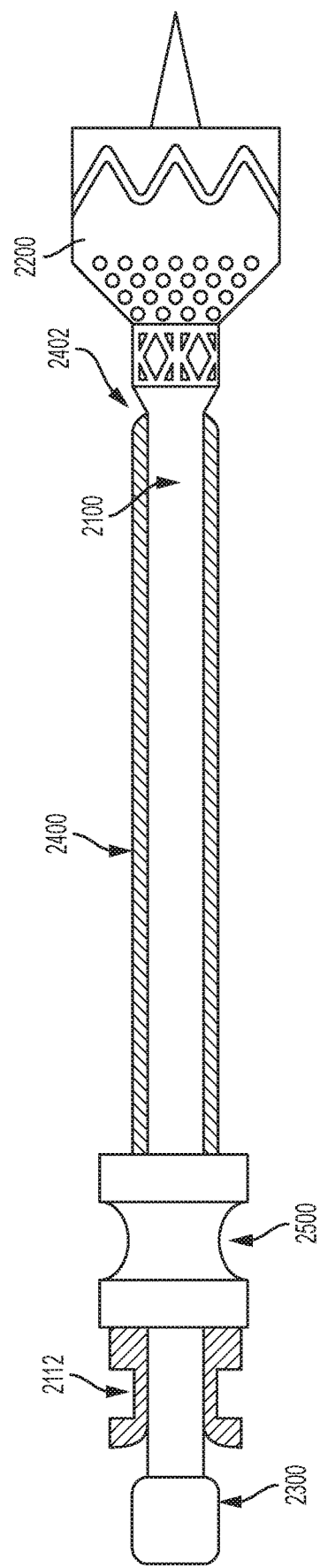
Figure 4C:
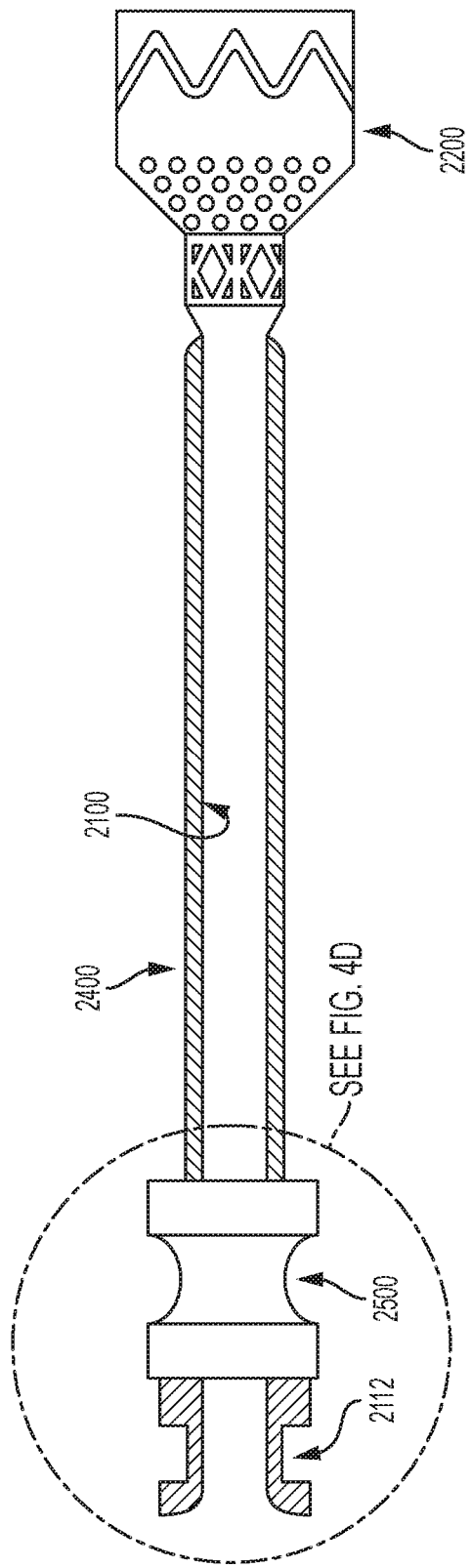

FIGS. 4A to 4C illustrate an embolic filter system 2000. FIG. 4A is illustrative of an exemplary embolic filter system 2000 shown in a delivery configuration. As discussed above, in some examples, the elongate element 2100 and the filter 2200 are mounted on an introducer 2300. The introducer 2300 having the elongate element 2100 and the filter 2200 mounted thereon is positioned within a constraining sheath such that the elongate element 2100 and/or the filter 2200 are configured for delivery to a target site within the patient's vasculature. Specifically, as illustrated in FIG. 4A, the filter 2200 is in a radially collapsed delivery configuration. As discussed above, in some examples, the elongate element 2100 and/or the filter 2200 can be advanced relative to the constraining member 2400 to facilitate delivery of the filter 2200 and the elongate element 2100 to the target site. In some examples, the constraining element 2400 is held fixed while the elongate element 2100 and/or the filter 2200 are advanced. In some examples, as explained above, the elongate element 2100 and/or the filter 2200 are advanced by way of advancing the introducer 2300 upon which the filter 2200 and/or elongate element 2100 are mounted.

FIG. 4B is illustrative of the exemplary embolic filter system 2000 after advancing the introducer 2300 distally relative to the constraining element 2400. Specifically, as shown, the introducer 2300 has been advanced relative to the constraining element 2400 such that the filter 2200 is advanced distally beyond a distal end 2402 of the constraining element 2400. Accordingly, with the filter 2200 having been advanced distally beyond a distal end 2402 of the constraining element 2400, the filter 2200 is free to expand to its radially expanded deployed configuration. Although, in some examples, removal of an additional constraining sheath may be required.

In some examples, after the filter 2200 has expanded to its radially expanded deployed configuration, the introducer 2300 can be withdrawn. That is, after the filter 2200 has expand to its radially expanded deployed configuration, the introducer 2300 can been withdrawn without displacing the position of the filter 2200 and/or the elongate element 2100 within the vasculature. In some examples, when the filter 2200 has expand to its radially expanded deployed configuration, the filter 2200 is no longer received or otherwise mounted on the filter mounting portion (e.g., the filter 2200 is no longer received within the circumferential relief). Thus, as the introducer is translated, no feature of the introducer (e.g., the filter mounting portion) engages the elongate element of the filter in a manner sufficient to cause the elongate element or the filter to translate with the introducer.

Turning now to FIG. 4C, the introducer 2300 has been withdrawn from the elongate element 2100 and the filter 2200. In some examples, with the introducer 2300 removed, blood flowing through vasculature within which the embolic filter system 2000 is deployed flows into the filter 2200 and/or the elongate element 2100. In some examples, this blood flow is sufficient to inflate or otherwise prevent the elongate element 2100 from collapsing under its own weight. That is, in examples where the elongate element 2100 is a soft and compliant material that is otherwise incapable of supporting its own weight, blood flowing into the elongate element 2100 applies a pressure on the inside of the lumen that is sufficient to inflate or otherwise prevent the elongate element 2100 from collapsing. As discussed above, the elongate element may include one or more blood-permeable areas. Likewise, although not illustrated, in some examples, the constraining element 2400 may be retracted along a portion of (or all of) the length of the elongate element 2100 such that blood may perfuse through the elongate element 2100 and reenter the vasculature. It will also be appreciated that, in some examples, the constraining element includes one or more blood permeable areas or regions.

In some examples, the embolic filter system 2000 includes a hemostatic sealing member 2500, as mentioned above. Generally, a hemostatic sealing member operates to maintain a hemostatic seal through which one or more medical devices can be passed while minimizing blood loss. Examples of hemostatic sealing members can be found in at least U.S. Pat. No. 9,314,605, issued on Apr. 19, 2016; and U.S. Patent Application Publication No. 2013/0123705, bearing Ser. No. 13/677,839, scheduled to issue on Feb. 7, 2017 as U.S. Pat. No. 9,561,347; the entire contents of each of which are incorporated herein by reference.

In some examples, the soft and compliant elongate element 2100 operates with the hemostatic sealing member 2500 to maintain a hemostatic seal while enabling one or more medical devices to be advanced through the working lumen of the elongate element 2100 to the treatment site as discussed above. Specifically, with reference to FIG. 4D, a cross sectional view of the hemostatic sealing member 2500 and the elongate element 2100 is illustrated. As shown, the hemostatic sealing member includes one or more pressurizable elements 2502 that operate to form a hemostatic seal inside of the hemostatic sealing member 2500. In some examples, these pressurizable elements 2502 of the hemostatic sealing member 2500 operate to collapse the soft compliant elongate element 2100 as it passes through the hemostatic sealing member 2500. In these examples, the pressure exerted on the inside of the elongate element 2100 by the blood therein is insufficient to overcome the pressure exerted by the pressurizable elements 2502 that operates to collapse the lumen 2108 of the elongate element 2100 in the region where it passes through the hemostatic sealing member 2500.

Figure 4D:
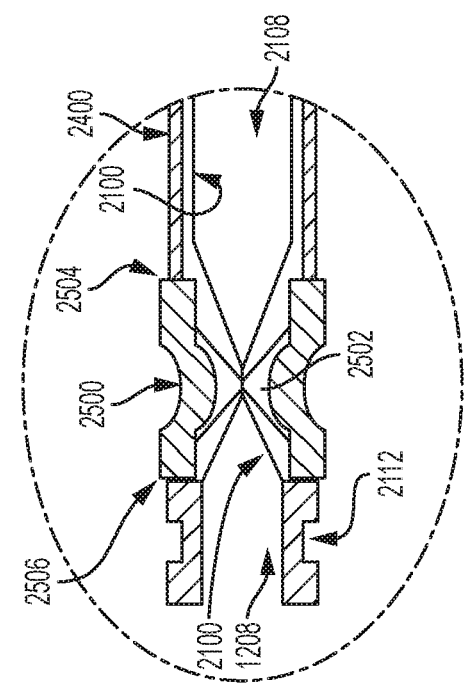
FIG. 4D is a detailed view of various components of the embolic filter system illustrated in FIGS. 4A-4C.

For example, as shown in FIG. 4D, the lumen 2108 of the elongate element 2100 is inflated on the distal side 2504 of the hemostatic sealing member 2500 by the pressure exerted on the inside of the lumen 2108 of the elongate element 2100 by the blood therein. Similarly, as shown, the elongate element 2100 is structurally supported by the stopping feature 2112 coupled to the material of the elongate element 2100 on the proximal side 2506 of the hemostatic sealing member 2500.

Those of skill in the art will appreciate that as a medical device is introduced into the lumen 2108 of the elongate element 2100 on the proximal side 2506 of the hemostatic sealing member 2500 and advanced therethrough to the distal side 2504, the pressurizable elements 2502 will apply a pressure to the elongate element 2100 and cause the elongate element 2100 to form a hemostatic seal between the interior of the lumen 2108 and the medical device being advanced therethrough.

Accordingly, the soft and compliant elongate element 2100 can be utilized in accordance with a hemostatic seal (such as the hemostatic seal referred to above) such that a hemostatic seal is formed by the lumen 2108 of the elongate element 2100 while maintaining the lumen 2108 as a working lumen through which one or more medical devices can be passed and delivered to a treatment site from a location outside of the patient's body. In some examples, the soft and compliant elongate element 2100 can be utilized in accordance with a hemostatic seal such that a hemostatic seal is formed both between the hemostatic seal and an exterior surface of the elongate element 2100 and within the lumen 2108 of the elongate element 2100 (e.g., by collapsing the interior lumen).

Figure 4E:
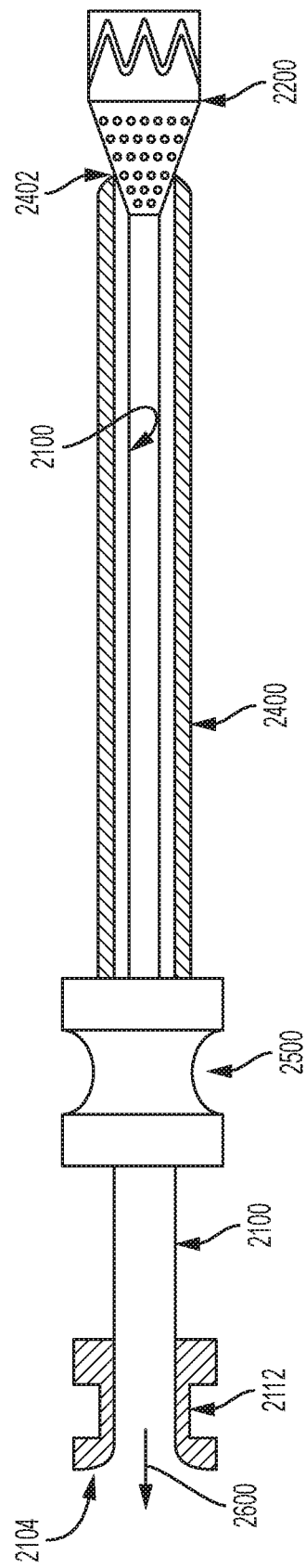
FIG. 4E is an illustration of an embolic filter system consistent with various aspects of the present disclosure.

Turning now to FIG. 4E, withdrawal of the elongate element 2100 and the filter 2200 is illustrated. In some examples, although an introducer 2300 is utilized when delivering the soft and compliant elongate element 2100 and filter 2200 to a target site within a patient's vasculature, the elongate element 2100 and the filter 220 can be withdrawn or otherwise removed therefrom without utilizing the introducer 2300. Specifically, in some examples, a tensile force 2600 can be applied to the proximal end 2104 of the elongate element 2100 to withdraw the elongate element 2100 and the filter 2200 from the target site. As discussed above, despite being soft and compliant, the elongate element 2100 is constructed of a material having a tensile strength sufficient to permit its withdrawal from the target site in such a manner as will be appreciated by those of skill in the art. In at least some examples, some contemplated materials are associated with tensile strength properties of between 1400-7000 psi. However, other materials having higher and lower tensile strengths are contemplated.

As shown in FIG. 4E, as the elongate element 2100 and the filter 2200 are withdrawn, the filter 2200 radially collapses as it is drawn into the constraining element 2400. In some examples, the constraining element 2400 is sufficiently rigid to cause the filter 2200 to radially collapse. In some examples, the embolic debris captured by the elongate element 2100 and the filter 2200 is retained with in the elongate element 2100 and the filter 2200 during removal of the elongate element 2100 and the filter 2200 from the vasculature. However, in some examples, the embolic debris captured within the filter 2200 and the elongate element 2100 can be additionally or alternatively aspirated prior to withdrawal. Such a configuration helps minimize the potential that the captured embolic debris will be released back into the vasculature as the filter 2200 and the elongate element 2100 are withdrawn.

In some examples, the elongate element 2100 and the filter 2200 can be withdrawn such the filter 2200 passes through the hemostatic sealing member 2500. In some examples, the hemostatic sealing member 2500 is coupled to the constraining member 2400. Thus, in some examples, the elongate element 2100 and the filter 2200 can be withdrawn from the vasculature independent of the withdrawal of the constraining element 2400. In some such examples, the hemostatic sealing member 2500 operates to minimize blood loss through the embolic filter system 2000 and maintain a hemostatic seal as the elongate element 2100 and the filter 2200 are drawn through the hemostatic sealing member 2500.

Figure 5A:
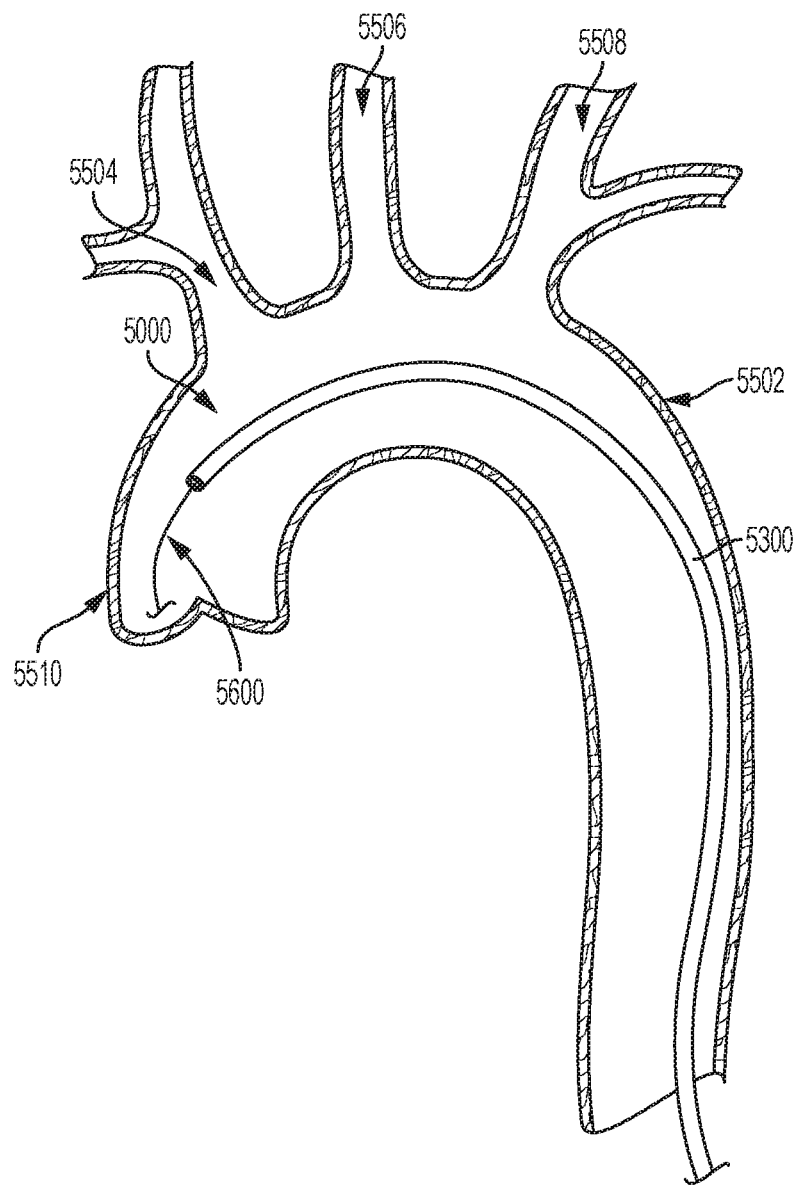
FIG. 5A is an illustration of an embolic filter system being delivered within the aortic arch consistent with various aspects of the present disclosure.

With reference now to FIG. 5A, an embolic filter system 5000 is illustrated in a delivery configuration in aortic arch 5502. The embolic filter system 5000 may be any of the embolic filter systems illustrated and described herein. As shown, the embolic filter system 5000 is advanced through the patient's vasculature to a target site. In this illustrated example, the embolic filter system 5000 is advanced to a location within the aortic arch 5502 at or proximate to the ascending aorta 5510. In some examples, the embolic filter system 5000 is in the delivery configuration as it is advanced through the patient's vasculature and delivered to the target site. As discussed in greater detail above, when in the delivery configuration, the elongate element and the filter are received (or at least partially received) within a constraining member, such as constraining element 5300. As shown, in some examples, the embolic filter system 5000 is guided along a guidewire 5600.

Figure 5B:
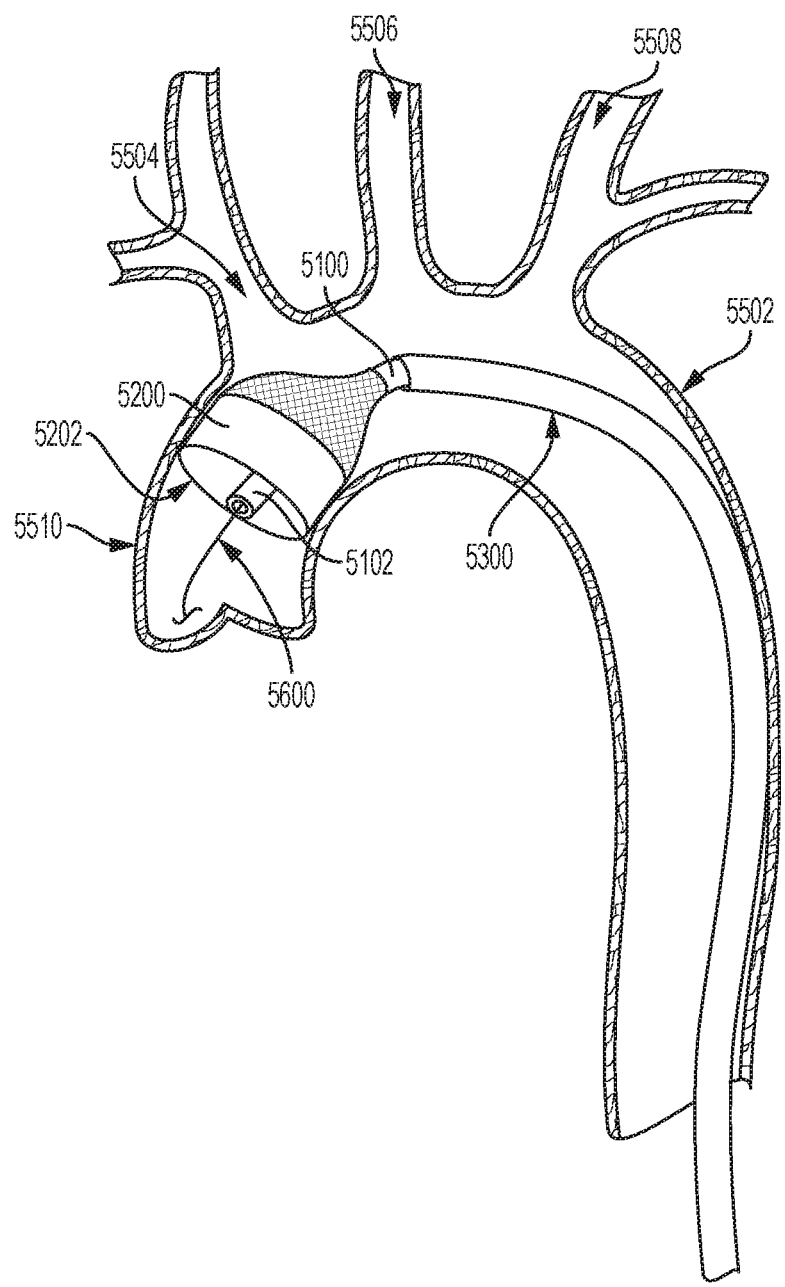
FIG. 5B is an illustration of an embolic filter system being deployed within the aortic arch consistent with various aspects of the present disclosure.

In some examples, after the embolic filter system is advanced to the target site, the filter and the elongate element are deployed. Turning now to FIG. 5B, the embolic filter system 5000 is illustrated partially deployed in aortic arch 5502. Specifically, the constraining element 5300 has been partially withdrawn to a position proximal to the proximal end of the filter 5200, and the filter 5200 has transitioned to its deployed configuration. In the deployed configuration, as shown in FIG. 5B, the distal end 5202 of the filter 5200 has a cross-sectional surface area substantially equal to that of the portion of the aorta within which the filter 5200 is deployed. In this illustrated example, the filter 5200 contacts some of or all of the wall of the region of the aortic arch 5502 where the filter 5200 is deployed. Consequently, the filter 5200 operates to direct the blood flowing from the ascending aorta 5510 into the filter 5200.

Figure 5C:
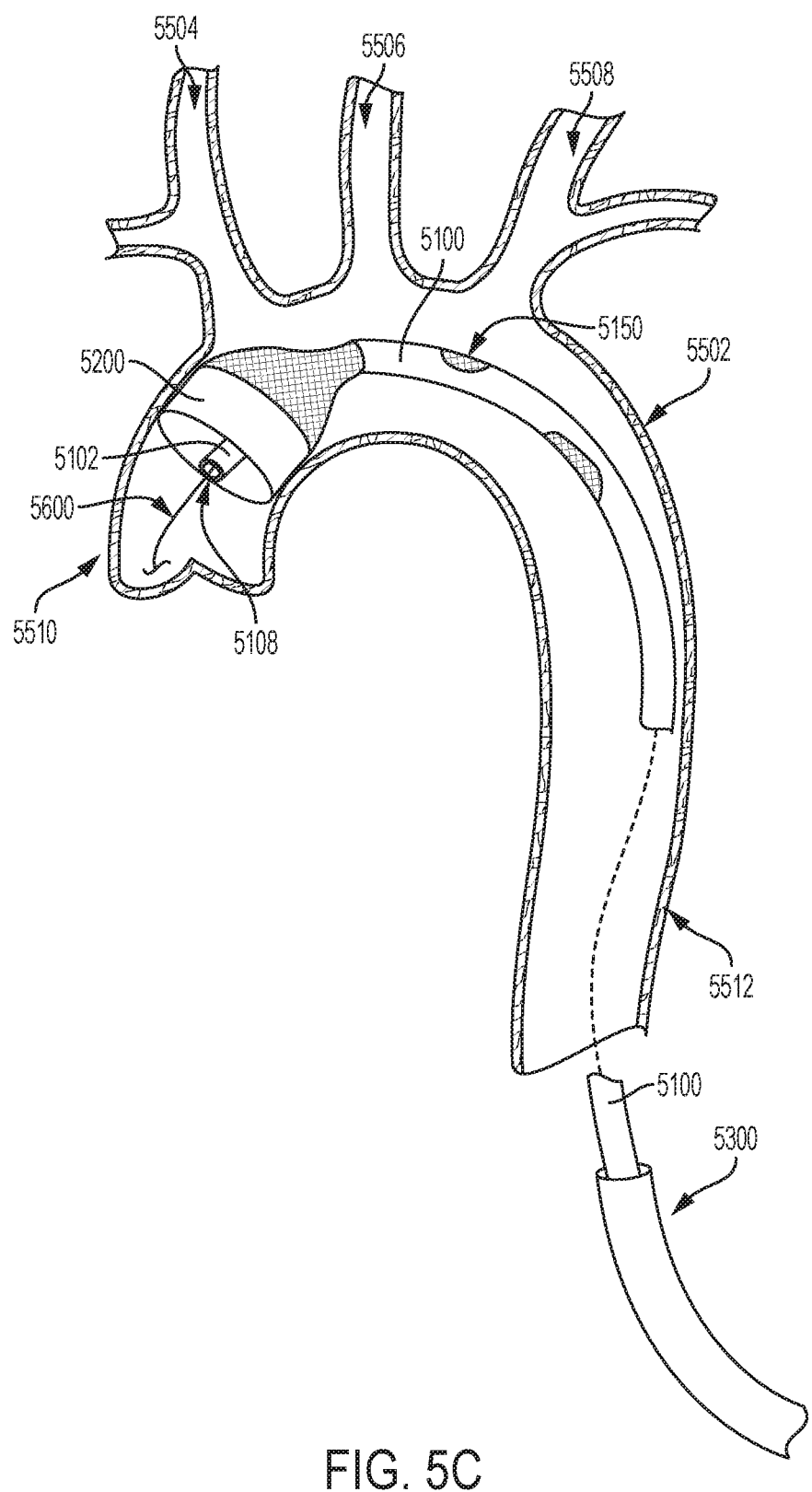
FIGS. 5C-5D include illustrations of an embolic filter system deployed in the aortic arch consistent with various aspects of the present disclosure.

FIG. 5C illustrates the filter 5200 and the elongate element 5100 with the constraining element 5300 withdrawn therefrom (or at least withdrawn to a position distal the aortic arch 5502). In some examples, because filter 5200 is blood-permeable, perfusion of blood to the brachiocephalic artery 5504, the carotid artery 5506, and the subclavian artery 5508, and perfusion through the aortic arch 5502 to the descending aorta 5512 and the downstream vasculature are possible. Additionally, the elongate element 5100 is illustrated as including a blood-permeable window 5150. Accordingly, perfusion of blood to at least the subclavian artery 5508 from the blood-permeable window 5150 is possible.

As discussed above, the degree of permeability of the embolic filter system may vary along a length of the filter and/or the elongate element. In the illustrated example of FIG. 5C, the blood-permeable window 5150 may be configured such that it is permeable to particles to which the filter is impermeable. Accordingly, larger particles that that did not permeate the filter 5200 may permeate the blood-permeable window 5150. As explained above, one methodology for achieving such a result includes configuring the filter with a plurality of first perforations having a first average size and configuring the blood-permeable window with a plurality of second perforations having second average size that is larger than the average size of the plurality of first perforations. Though certain of the above-discussed examples include a filter (e.g., 1200) that has some degree of permeability to blood, in some examples, the filter may be impermeable to blood such that the filter operates instead as a deflector that funnels the blood and other media (e.g., embolic debris) into the elongate element.

Figure 5D:
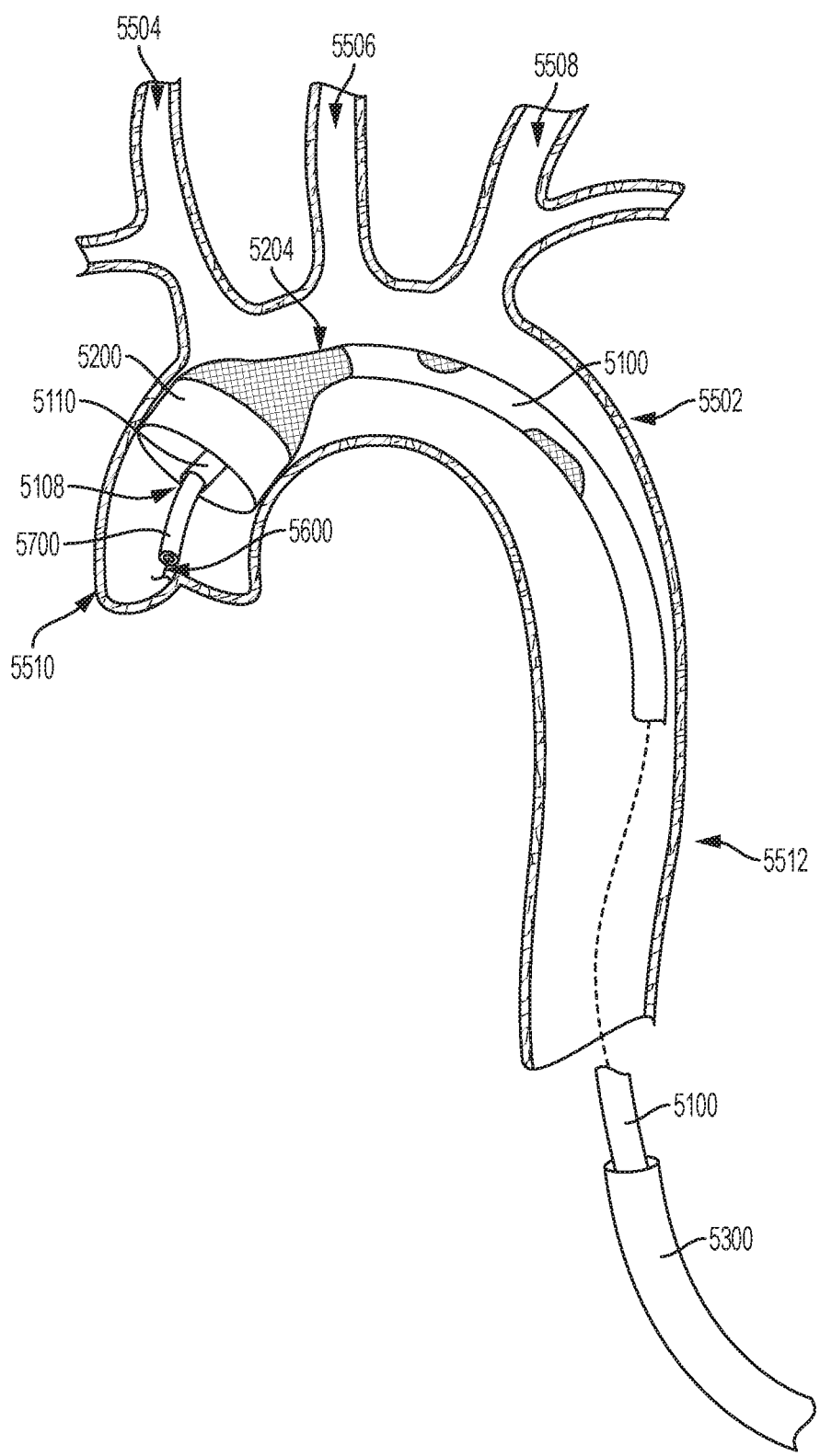

As discussed above, in some examples, a distal portion of the elongate element may extend distally of the proximal end of the filter and may operate as a working lumen. In the illustrated example of FIG. 5D, a distal portion 5110 of the elongate element 5100 extends distally of the proximal end 5204 of the filter 5200. As shown, the working lumen 5108 of the elongate element 5100 provides a mechanism for delivery of one or more medical devices to the treatment site, such as medical device 5700. In the illustrated example of FIG. 5D, the distal portion 5110 operates to prevent entanglement between the medical device 5700 and the filter 5200, as explained above.

As discussed above, in various examples, the elongate element and/or the filter operate to filter embolic debris and other blood media from the patient's blood. In some such examples, the elongate element and/or the filter is formed of a sufficiently permeable material and/or includes one or more perforations. Likewise, as mentioned above, in some examples, the elongate element and/or the filter is configured such that the elongate element and/or the filter is permeable (e.g., blood permeable) at one or more discrete locations. In some examples, the elongate element and/or the filter can be configured such that it is blood-permeable in some locations and blood impermeable in other locations. In some examples, the elongate element and/or the filter includes one or more filtering windows configured to further filter the blood and embolic debris.

Generally, permeable windows (e.g., blood-permeable) can be located anywhere along or about the elongate element or filter and can comprise various suitable dimensions (including, but not limited to circular, ovoidal, elongated, spiral, random, etc.). In some examples, an elongate element or filter can comprise at least one window having a greater porosity than an adjacent portion of the elongate element or filter.

In various examples, one or more permeable windows (e.g., blood-permeable) can be used to reduce or eliminate the likelihood of a stagnant column of blood within the elongate element or the filter. If instance, in some examples, trapped embolic debris which are rendered stagnant can decrease porosity and increase the pressure gradient across the elongate element or the filter. In turn, embolic debris which are rendered stagnant can, over time, build up and decrease filtering efficiency, which may be especially problematic. An elongate element having one or more permeable windows (e.g., blood-permeable) on the other hand, can allow blood and redirected embolic debris to migrate down and into its lumen, where it's collection will have no detrimental effect on filtering efficiency, and where it's removal by aspiration can be accomplished by the operator.

In various examples, a permeable window can comprise a one-way flap or valve to permit perfusion of blood therethrough yet prevent blood from entering, for example, during an aspiration procedure. In some examples, a one-way valve can comprise a biocompatible material (e.g., a fluoropolymer) having one or more slits and being biased to open in one direction. In some examples, a one-way flap can comprise a biocompatible material (e.g., a fluoropolymer) with a support frame. In some examples, a one-way flap or valve can be positioned on the outer and/or inner surface of a permeable window (e.g., blood-permeable) in such a manner as to substantially cover the window.

As discussed above, in various examples, the filter includes a structural element. In various examples the structural element is comprised of one or more support elements, such as one or more braids, meshes, lattices, wires, rings, struts, or any other suitable support element. In some examples, the support elements are tubular and may be laser cut or formed separately. In some examples, one or more of the support elements may be formed of a shape-memory material such as nitinol, such that the structural element is a self-expanding structural element as would be appreciated by those of skill in the art. In other examples, however, one or more of the support elements may be formed from other resilient metals that may be expandable through the use of an expansion aid (such as a balloon). For example, one or more of the support elements may be formed from a polymer or a biocompatible metallic alloy such as stainless steel.

Moreover, those of skill will appreciate that the configurations discussed herein a scalable in that they can be scaled up or scaled down for different applications. That is, while certain of the configurations discussed herein are illustrated and described in association with placement within the aortic arch, the versatility of the system provides for implementation in virtually any other area of the patient's vasculature. For example, the various configurations discussed herein may be scaled for application within various peripheral vessels and lumens such as the brachiocephalic artery, and/or the carotid artery, and/or the subclavian artery. Likewise, as it relates to the aortic arch, the present disclosure can be used in connection with femoral, transapical and thoracotomy approaches. Moreover, this disclosure should not be interpreted as limiting application to the vessels proximate the heart. For instance, the devices and systems described herein may be implemented throughout the vasculature of the body including vasculature above and below the heart to prevent the migration of embolic debris during various other revascularization procedures. Additionally, the embodiments can be used in connection with not just humans, but also various organisms having mammalian anatomies. Thus, it is intended that the embodiments described herein cover the modifications and variations within the scope of this disclosure.

Additionally, in some examples, more than one device or system may be deployed for a given procedure. For instance, in some cardiac procedures, one of the devices described herein may be placed in the aortic arch, and/or the brachiocephalic artery, and/or the carotid artery, and/or the subclavian artery.

Turning now to FIGS. 6A and 6B, an embolic filter system 6000 is illustrated. In various examples, the embolic filter system 6000 includes first elongate element 6100, a filtering portion 6200, and a second elongate element 6300. As shown, the embolic filter system 6000 includes a distal end 6002 and a proximal end 6004. Likewise, in some examples, the first elongate element 6100 includes a distal end 6102 (obstructed from view by the distal end of the second elongate element 6300) and a proximal end 6104, and the second elongate element 6300 includes a distal end 6302 and a proximal end 6304. In various examples, each of the first and second elongate elements has lumens extending therethrough. For example, the first elongate element includes an inner lumen 6106 and the second elongate element includes an inner lumen 6306 (obstructed from view). In some examples, the inner lumen 6106 of the first elongate element operates as a working lumen as described herein.

In some examples, the first elongate element 6100 is positioned within the inner lumen of the second elongate element 6300 such that the first and second elongate elements 6100 and 6300 are coaxial. As shown in FIGS. 6A and 6B, the first elongate element 6100 extends between the distal and proximal ends of the second elongate element 6300. In some examples, the distal end 6102 of the first elongate element 6100 is aligned with the distal end of the second elongate element.

In some examples, the second elongate element 6300 is a longitudinally extending structure having a lumen extending therethrough, as mentioned above. In some examples, the second elongate element 6300 includes a deployable filtering portion 6200 including one or more support element, such as support element 6202A, 6202B, 6202C, 6202D, 6202E, and 6202F (obstructed from view). Generally, the support elements are evenly distributed about the second elongate element 6300. In some examples, the support elements are formed in the wall of the second elongate element 6300. In some such examples, one or more slits or cut lines are formed in the wall of the second elongate element 6300. The slits or cut lines extend longitudinally along a portion of the second elongate element 6300. A support element is formed between adjacent longitudinally extending slits. Generally, the slits penetrate from an exterior surface to the inner lumen of the second elongate element 6300.

In some examples, the support elements extend from a position proximal of the distal end 6302 of the second elongate element 6300 to a position proximal thereto as shown. That is, each of the support elements has a distal end, a proximal end, and an intermediate portion extending therebetween. In some examples, a length of the support elements is measure between the distal and proximal ends of the support elements. In some examples, the distal and proximal ends of the support elements terminate into the second elongate element 6300 as explained further below.

In some examples, a blood-permeable membrane 6204 (such as the membranes discussed above) is disposed about the support elements or a portion thereof. In some examples, a distal edge of the blood-permeable membrane is positioned along the intermediate portion of the support elements. In some examples, a proximal edge of the blood-permeable membrane is positioned at or proximal to the proximal ends of the support elements. That is, in some examples, the blood-permeable membrane extends from a position along the support elements proximal to the distal ends of the support elements to the proximal ends of the support elements or proximal thereof. In some examples, as explained further below, the support elements and the blood-permeable membrane operate to filter embolic debris from the blood.

In some examples, the blood-permeable membrane is coupled or otherwise secured to the elongate element at or proximal to the proximal ends of the support elements. In some examples, the blood-permeable membrane is additionally coupled or otherwise secured to the intermediate portion of the support elements, however it need not be. In some other examples, the blood-permeable membrane includes one or more tethers that extend from the distal edge of the blood-permeable membrane to a position along either the support elements or a portion of the second elongate element 6300 distal thereof. For instance, as shown in FIGS. 6A and 6B the second elongate element 6300 includes a distal portion 6308 that extends between the distal end 6302 of the elongate element and the distal ends of the support elements. In some examples, the support elements terminate proximal of the distal portion 6308 such that the distal portion 6308 is free from slits.

In some examples, the first and second elongate elements 6100 and 6300 are secured or otherwise coupled to one another at the distal portion 6308. In some examples, the first and second elongate elements 6100 and 6300 are secured or otherwise coupled together such that the distal ends thereof are constrained against relative axial translation. In some such examples, the portions of the first and second elongate elements 6100 and 6300 proximal to the distal portion 6308 are free to translate axially (or slide) relative to one another. As explained further below, the filtering portion of the embolic filter system 6000 is deployed by sliding the proximal end 6304 of the second elongate element 6300 relative to the proximal end 6104 of the first elongate element 6100.

In various examples, the embolic filter system 6000 can be deployed within a region of a patient's vasculature such that the embolic filter system 6000 operates to filter embolic debris from the blood flowing through that region. In some such examples, the embolic filter system 6000 is transitionable between deployed and delivery configurations, as explained in greater detail below. FIG. 6A illustrates the embolic filter system 6000 in the delivery configuration while FIG. 6B illustrates the embolic filter system 6000 in the deployed configuration. In various examples In some examples, in the delivery configuration, the embolic filter system 6000 maintains a minimal delivery profile. However, when transitioned to the deployed configuration, a filtering portion of the embolic filter system 6000 expands to occupy a portion or all of the cross sectional area of a vessel within which it is deployed (similar to the other embolic filter systems described herein). In some examples, in the deployed configuration, the support element (6202A-6202F) or a portion thereof are deflected away from a longitudinal axis of the second elongate element 6300.

In some examples, the embolic filter system 6000 is transitioned to the deployed configuration by distally axially translating or sliding the proximal end 6304 of the second elongate element 6300 relative to the proximal end 6104 of the first elongate element 6100. In some examples, the embolic filter system 6000 is transitioned to the deployed configuration by additionally or alternatively proximally axially translating or sliding the proximal end 6104 of the first elongate element 6100 relative to the proximal end 6304 of the second elongate element 6300. It will be appreciated that, in some examples, the embolic filter system 6000 is likewise deployable by proximally translating or sliding the proximal end 6104 of the first elongate element 6100 while maintaining a constant (or substantially constant) position of the proximal end 6304 of the second elongate element 6300. Likewise, in some examples, the embolic filter system 6000 is deployable by distally translating or sliding the proximal end 6304 of the second elongate element 6300 while maintaining a constant (or substantially constant) position of the proximal end 6104 of the first elongate element 6100.

Those of skill in the art will appreciate that, because the first and second elongate elements 6100 and 6300 are secured together at the distal portion 6308, as the proximal end 6304 of the second elongate element 6300 translates distally relative to the proximal end 6104 of the first elongate element 6100, one or more of the first and second elongate element 6100 and 6300 must buckle. In this regard, the support elements of the second elongate element 6300 are configured to deflect away from the longitudinal axis of the second elongate element 6300. For example, as illustrated in FIG. 6B, the support elements (6202A-6202F) bow, buckle, or otherwise deflect as a result of the proximal end 6304 of the second elongate element 6300 translating distally relative to the proximal end 6104 of the first elongate element 6100.

This deflection of the support elements operates to expand the blood-permeable membrane 6204 within the vessel within which the embolic filter system 6000 is deployed. Although obstructed from view in FIG. 6B, in some examples, the portion of the first elongate element 6100 extending beneath the support elements of the second elongate element 6300 may include one or more apertures (similar to apertures 1112) that operate to allow embolic debris trapped by the blood-permeable membrane to be transferred into the lumen 6106 of the first elongate element 6100 as the embolic filter system 6000 is transitioned from the deployed configuration to the delivery configuration upon removal from the vasculature. In some examples, such apertures are positioned along the first elongate element proximal to the position of the distal edge of the blood-permeable membrane 6204 when the embolic filter system 6000 is in the deployed configuration. Such a configuration ensures that embolic debris escaping from the lumen 6106 is captured and retained by the blood-permeable membrane 6204.

In some other examples where the first elongate element is free of apertures in portion of the first elongate element 6100 extending beneath the support elements of the second elongate element 6300, any embolic debris captured by the blood-permeable membrane 6204 is trapped between the blood-permeable membrane (and/or the support elements) and the exterior of the portion of the first elongate element 6100 extending beneath the support elements of the second elongate element 6300 as will be appreciated by those of skill in the art.

In some examples, the embolic filter system 6000 is transitioned from the deployed configuration to the delivery configuration by proximally axially translating or sliding the proximal end 6304 of the second elongate element 6300 relative to the proximal end 6104 of the first elongate element 6100. In some examples, the embolic filter system 6000 is transitioned from the deployed configuration to the delivery configuration by additionally or alternatively distally axially translating or sliding the proximal end 6104 of the first elongate element 6100 relative to the proximal end 6304 of the second elongate element 6300. It will be appreciated that, in some examples, the proximal end 6104 of the first elongate element 6100 may be proximally axially translated while maintaining a constant (or substantially constant) position of the proximal end 6304 of the second elongate element 6300. Likewise, in some examples, the proximal end 6304 of the second elongate element 6300 may be distally axially translated while maintaining a constant (or substantially constant) position of the proximal end 6104 of the first elongate element 6100.

Although the embolic filter system 6000 is illustrated and described as including 6 support elements (6202A-6202F), it should be appreciated that the embolic filter system 6000 may include any number of support elements. Likewise, although the support elements are illustrated as being evenly distributed about the second elongate element 6300, it should be appreciated that the support elements are disproportionately distributed. Likewise, the support elements need not all be of equal size (length and/or width).

As mentioned above, in some examples, the system may include one or more steering lines (or wires). Thus, in some examples, the system is steerable. In some examples, the one or more steering lines are coupled to a distal end of the elongate element. With reference to FIG. 1B, in some examples, the one or more steering lines may be coupled to the distal portion 1110 of the elongate element 1100, or alternatively or additionally to the distal end 1102 of the elongate element. Thus, in some examples, the one or more steering lines are coupled to the elongate element at a location that is distal the proximal end of the filter (such as the proximal end 1204 of the filter 1200). Such a configuration provides for enhanced steering capability or deflectability of the distal end of the system, which when navigating tortuous areas of the vasculature provides for increased control and helps minimize the risk of damaging a vessel.

In some examples, the elongate element and/or the deflector can be housed in a sleeve, sheath, sock or other constraining mechanism. Such a constraining mechanism (and/or the elongate element and/or the deflector itself) can have a deployment line which, if locked (e.g., pin, wire or other), acts as a tension line (that operates as a steering line) to cause bending of the elongate element and/or the deflector. In some such examples, the sleeve, sheath, sock or other constraining mechanism within which the elongate element is house generally terminates proximal of the area at which the steering line (i.e., locked deployment line or tension line) is coupled to the elongate element. Such a configuration provides that the elongate element and the steering line can form a bow and string configuration as tension is applied to the steering line, which in turn deflects the distal end of the system. Those of skill will appreciate that steerable embodiments can be particularly beneficial in treating the aortic arch or other tortuous vasculature. Steerable embodiments can be particularly useful in preventing the deflector from compressing against the outside of a bend in a tortuous anatomy. Such steerable embodiments can also be useful in creating an exit from the elongate element that is substantially aligned with the axis of the vessel and the axis of the deflector mechanism.

Figure 7:
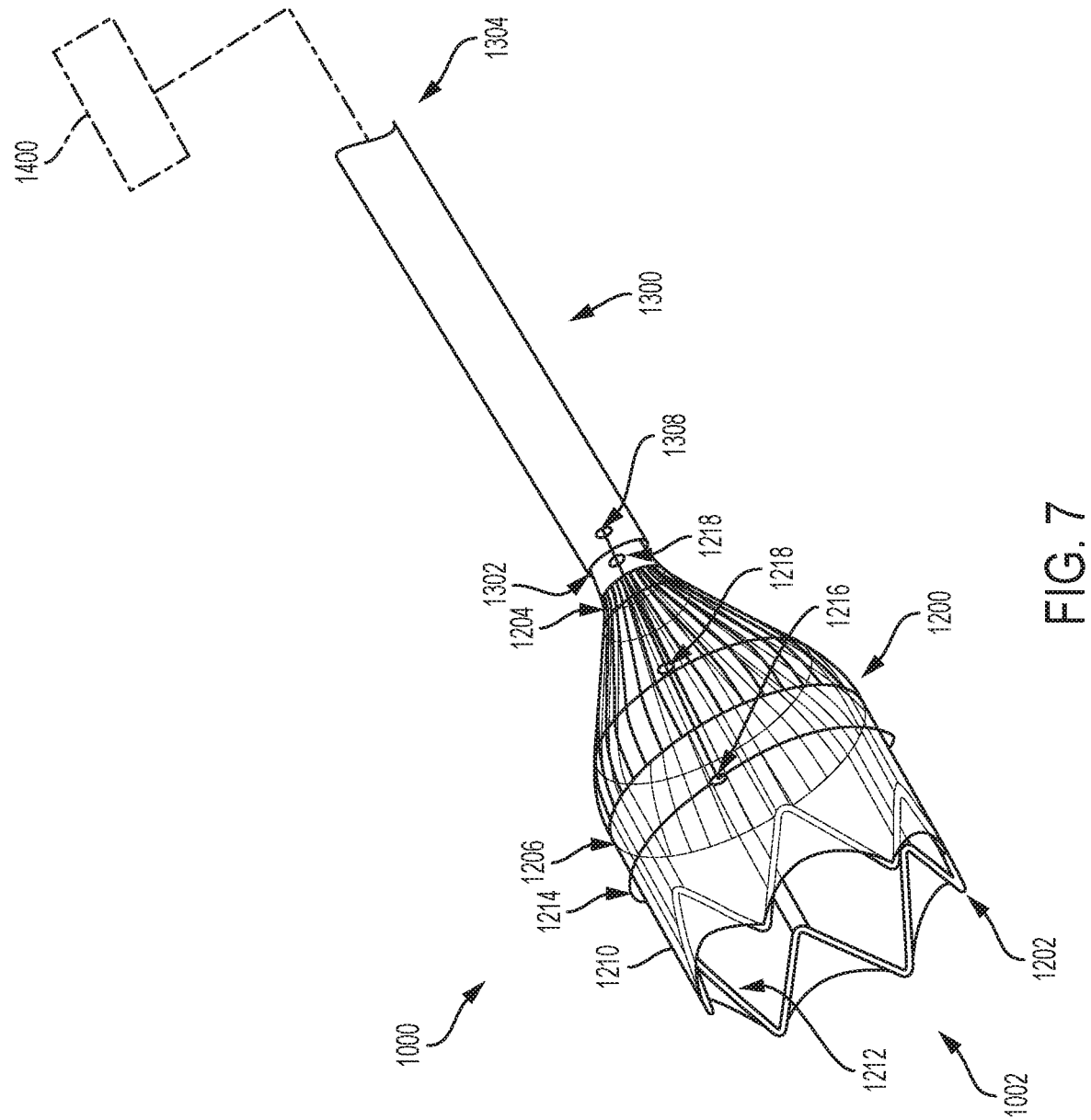
FIG. 7 is an illustration of an embolic filter system consistent with various aspects of the present disclosure.

In some examples, the embolic filter system 1000 includes one or more features that operate to help transition the embolic filter system 1000 between a deployed configuration and delivery/removal configurations. Though not equivalents, in some examples, such features may be implements in addition to or as an alternative to the constraining element 1300. For instance, as shown in FIG. 7, in some examples, the embolic filter system 1000 includes one or more constraining elements, such as a constraining fiber 1214. The constraining fiber 1214 is generally operable to control expansion and/or collapse of the filter 1200. In various examples, the constraining fiber 1214 is routed about a circumference of the filter 1200 such that a length of the constraining fiber 1214 extending about the circumference of the filter 1200 can be reduced and/or increased to constrain or unconstrain the filter 1200, and thereby transition the filter between collapsed and expanded states as those of skill will appreciate.

As shown in FIG. 7, the constraining fiber 1214 is routed circumferentially about an exterior surface of the filter 1200. It will be appreciated, however, that the constraining fiber 1214 may alternatively be routed about an interior surface of the filter 1200, or alternatively may be routed such that that the constraining fiber 1214 traverses along one or more portions of both the interior and exterior surfaces of the filter 1200. For instance, in some examples, the filter 1200 may include a plurality of perforations that are arranged about a circumference of the filter 1200. In some such examples, the constraining fiber 1214 is routed through the various perforations such that the constraining fiber 1214 extends circumferentially about the filter 1200, as those of skill will appreciate. The constraining fiber 1214 may extend about an exterior of the structural support 1212 in any of the above-referenced configurations. Alternatively, in some examples, the constraining fiber 1214 extends about an interior of the structural support 1212. Still further, in some examples, the constraining fiber 1214 may be routed such that it extends about one or more portions of both the interior and exterior of the structural support 1212.

In some examples, the constraining fiber 1214 is routed through one or more features of the filter 1200 that define a designated path along and/or about the filter 1200. For example, as shown in FIG. 7, the embolic filter system 1000 includes one or more routing conduits 1218 that extend along one or more portion of the embolic filter system 1000. In some examples, one or more routing conduits 1218 extend along an interior and/or exterior of the constraining element 1300. In some example, the one or more routing conduits 1218 extend along an interior and/or exterior of the filter 1200 consistent with the discussion above. In various example, the constraining fiber 1214 is routed through such routing conduits 1218 and is in a sliding relation thereto. Thus, it will be appreciated that while the routing conduits 1218 generally constrain a routing path of the constraining fiber 1214, the constraining fiber 1214 is nevertheless free to slide within (e.g., relative to) such routing conduits 1218. While the routing conduits 1218 are illustrated in FIG. 7 as extending longitudinally along the filter 1200, in various examples, one or more routing conduits may extend circumferentially (partially or entirely) about the filter 1200.

In various examples, the constraining fiber 1214 extends longitudinally from a proximal end of the embolic filter system 1000, such as from a handle 1400 or other control mechanism as those of skill will appreciate. As shown in FIG. 7, the constraining fiber 1214 extends through an interior region of the embolic filter system 1000, through an aperture 1308, and along an exterior surface of the filter 1200. In some examples, the constraining fiber 1214 extends through one or more portions of an interior lumen of the elongate element 1100. In some examples, the constraining fiber alternatively or additionally extends through one or more portions of an interior lumen of the constraining element 1300. Thus, in some examples, the constraining fiber 1214 extends within an annular region defined between the constraining element 1300 and the elongate element 1100. Moreover, while the constraining fiber 1214 is illustrated as extending through an aperture 1308 in the constraining element 1300, in some examples, the constraining fiber 1214 extends from the distal end 1302 of the constraining element 1300 (or alternatively from the distal end 1102 of the elongate element 1100).

In various examples, the constraining fiber 1214 forms a loop about the circumference of the filter 1200 such that a diameter of the loop can be reduced or expanded to constrain and/or unconstrain the filter 1200 as those of skill should appreciate. In some example, a distal end of the constraining fiber 1214 include an eyelet 1216 or other feature that facilitates hitching of the constraining fiber 1214 upon itself such that a tension applied to the constraining fiber 1214 can be varied to cause a resulting variance in the diameter of the loop. Some examples, the constraining fiber 1214 may be used in combination with a lockwire. For instance, in some examples, a portion of the constraining fiber 1214, such as a distal end eyelet, is constrained by an engagement with the lockwire. Such engagement with the lockwire permits a tension to be applied and removed from the constraining fiber 1214 without causing the constraining fiber 1214 to be removed from its position about the filter 1200. In some such examples, the constraining fiber 1214 extends about the filter 1200, hitches upon itself, and extends to a position where it engages with the lockwire. In some examples, upon withdrawal of the lockwire, the constraining fiber 1214 is disengaged from the lockwire and can be withdrawn from about the filter 1200.

As discussed above, in some examples, the elongate element 2100 lacks sufficient structural rigidity to support its own weight, has little to no column strength, and/or is not generally torqueable, yet exhibits good tensile strength. In some other examples, the elongate element 2100 may include one or more structural elements or components that afford it sufficient structural integrity such that the elongate element 2100 is advanceable within an introduction sheath and/or a constraining element, such as constraining element 2400. That is, in some examples, the elongate element is comprised of both a structural element and a covering material. The structural element and the covering material are consistent with those discussed herein. By providing an elongate element 2100 with a structural element, the elongate element 2100 can be introduced into the vasculature without the added requirement of an introducer. In particular, the structural element of the elongate element 2100 in combination with the covering material provides for a construct that can be advanced (e.g., is pushable) within an introducer sheath and/or a constraining sheath. That is, applying a distally directed force to the proximal end of the elongate element 2100 will operate to cause the elongate element 2100 (and the filter 2200) to translate distally despite the embolic filter system 2000 not being mounted on an introducer.

In some examples, such a configuration provides for a system having a delivery profile that is smaller in comparison to convention designs because, in some examples, the elongate element 2100 can be radially collapsed upon itself instead of being compressed onto an introducer or delivery catheter, as those of skill will appreciate. Likewise, by being pushable within an introducer sheath and/or within a constraining sheath, the elongate element 2100 does not require additional components for delivery, which reduces system costs, procedure time, and risk to the patient.

Figure 8:
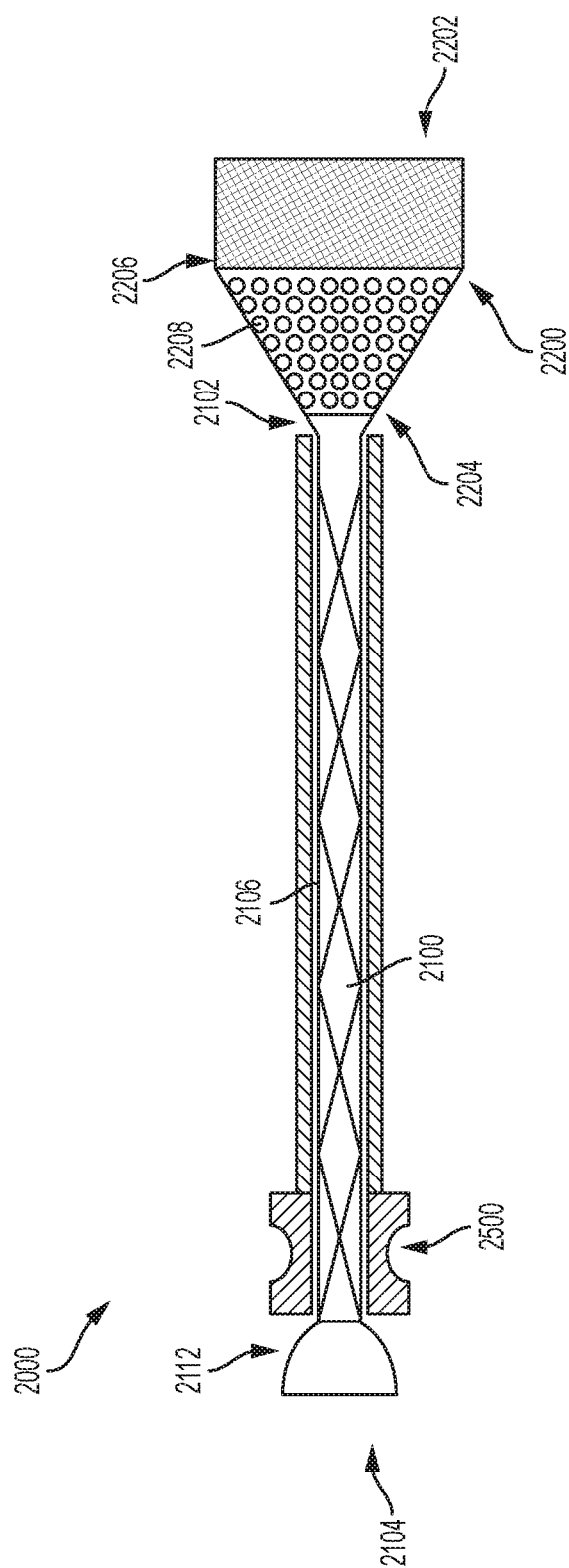
FIG. 8 is an illustration of an embolic filter system consistent with various aspects of the present disclosure.

With reference to FIG. 8, in some such examples, the embolic filter system 2000 includes an elongate element 2100 having a structural element, such as a braided element. In some examples, the braided element includes a nitinol wire, though other materials, including those discussed herein, are contemplated. In some examples, the braided element is covered with a suitable covering material (e.g., a filter material), such as ePTFE or any other suitable material as discussed herein to form the elongate element 2100. In some examples, the covering material of the elongate element 2100 is blood permeable. In other examples, the covering material of the elongate element 2100 is blood impermeable. In some examples, the blood impermeable covering material of the elongate element is modified consistent with the discussion herein such that blood is operable to flow through the perforations. In some such examples, the perforations are sized to prevent the passage of embolic debris in excess of a designated threshold size. For instance, as mentioned herein, the perforations may be between 50 microns and 1000 microns depending on the particular application. It will also be appreciated that the elongate element may be configured such that blood is operable to pass or flow through one or more portions of the elongate element 2100 while being prevented from flowing through one or more other portions of the elongate element 2100 as those of skill will appreciate.

Additionally, as shown in FIG. 8, the embolic filter system 2000 includes a filter 2200. The filter 2200 generally includes a braided structural support 2212 and a covering material consistent with the discussion above. In some examples, the covering material of the filter 2200 is the same as the covering material of the elongate element 2100. In some examples, the structure support of the filter 2200 is the same as the structural support of the elongate element. In some examples, the covering material of the filter 2200 is blood permeable. In other examples, the covering material of the filter 2200 is blood impermeable. In some examples, the blood impermeable covering material of the filter 2200 is modified consistent with the discussion herein such that blood is operable to flow through the perforations. In some such examples, the perforations are sized to prevent the passage of embolic debris in excess of a designated threshold size as discussed herein. It will also be appreciated that the elongate element may be configured such that blood is operable to pass or flow through one or more portions of the filter 2200 while being prevented from flowing through one or more other portions of the filter 2200 as those of skill will appreciate.

Numerous characteristics and advantages have been set forth in the preceding description, including various alternatives together with details of the structure and function of the devices and/or methods. Moreover, the inventive scope of the various concepts addressed in this disclosure has been described both generically and with regard to specific examples. The disclosure is intended as illustrative only and as such is not intended to be exhaustive. For example, the various embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An embolic filter comprising:
   an elongate element having a proximal end and a distal end, the elongate element including a first structural element and a first covering material, the elongate element having sufficient structural integrity to support being advanced within a delivery sheath; and
   a filter portion positioned such that the distal end of the elongate element extends beyond the filter portion, the filter portion including a second structural element and a second covering material, wherein a portion of the second covering material includes a plurality of perforations configured to filter embolic debris from blood flowing into the filter portion; wherein a distally directed force applied to the proximal end of the elongate element is operable to cause a distal translation of the elongate element and the filter portion to the delivery sheath.

2. The embolic filter of claim 1, wherein the first structure element is a self-expanding wire braid.

3. The embolic filter of claim 1, wherein the elongate element has sufficient structural integrity to support being advanced within the delivery sheath without requiring an introducer.

4. The embolic filter of claim 1, wherein the filter portion is blood permeable and wherein the plurality of perforations have an average size of one hundred microns.

5. The embolic filter of claim 1, wherein the second covering material of the filter portion is blood impermeable, and wherein plurality of perforations are formed in the second covering material such that blood is operable to flow through the second covering material of the filter portion.

6. The embolic filter of claim 1, wherein the elongate element is blood impermeable.

7. The embolic filter of claim 1, wherein the elongate element is configured to be advanced through a valve that operates to control a flow of blood through a lumen of the elongate element during a clinical procedure.

8. The embolic filter of claim 1, wherein one of the first and second covering materials include ePTFE.

9. An endoprosthesis delivery device comprising:
   an expandable filter element mounted on a catheter shaft, having a capture area within the expandable filter element when the expandable filter element is deployed;
   an elongated conduit configured such that a leading end of the elongated conduit extends through and beyond the expandable filter element when the expandable filter element is deployed at a treatment site, the elongated conduit configured to allow for delivery of an endoprosthesis beyond the expandable filter element; and
   wherein the elongated conduit includes at least one aperture through a side wall providing fluid communication between the capture area and an interior of the elongated conduit; wherein the elongated conduit and the catheter shaft form a single monolithic unit.

10. The device of claim 9, wherein the elongated conduit extends from the catheter shaft.

11. The device of claim 9, wherein the at least one aperture is configured to facilitate a transfer of embolic debris captured within the filter to the elongated conduit.

* * * * *